United States Patent
Albert et al.

(10) Patent No.: US 9,254,092 B2
(45) Date of Patent: Feb. 9, 2016

(54) SYSTEMS AND METHODS FOR PROCESSING AND ANALYZING MEDICAL DATA

(71) Applicant: AliveCor, Inc., San Francisco, CA (US)

(72) Inventors: David E. Albert, Oklahoma City, OK (US); Judy Wade, San Francisco, CA (US)

(73) Assignee: ALIVECOR, INC., San Francisco, CA (US)

( * ) Notice: Subject to any disclaimer, the term of this patent is extended or adjusted under 35 U.S.C. 154(b) by 0 days.

(21) Appl. No.: 14/217,032

(22) Filed: Mar. 17, 2014

(65) Prior Publication Data

US 2014/0276162 A1  Sep. 18, 2014

Related U.S. Application Data

(60) Provisional application No. 61/800,879, filed on Mar. 15, 2013.

(51) Int. Cl.
| | |
|---|---|
| A61B 5/04 | (2006.01) |
| G06Q 50/24 | (2012.01) |
| G06F 19/00 | (2011.01) |
| G06Q 50/22 | (2012.01) |
| G06Q 50/18 | (2012.01) |

(52) U.S. Cl.
CPC ............ *A61B 5/04012* (2013.01); *G06F 19/327* (2013.01); *G06F 19/3418* (2013.01); *G06Q 50/188* (2013.01); *G06Q 50/22* (2013.01); *G06Q 50/24* (2013.01)

(58) Field of Classification Search
CPC .............. A61B 5/04012; G06F 19/327; G06F 19/3418; G06Q 50/22; G06Q 50/24
See application file for complete search history.

(56) References Cited

U.S. PATENT DOCUMENTS

| | | |
|---|---|---|
| 3,717,857 A | 2/1973 | Evans |
| 3,731,311 A | 5/1973 | Williams |

(Continued)

FOREIGN PATENT DOCUMENTS

| | | |
|---|---|---|
| CH | 675675 A5 | 10/1990 |
| CN | 101828915 A | 9/2010 |

(Continued)

OTHER PUBLICATIONS

Albert, David E.; U.S. Appl. No. 14/252,044 entitled "Cardiac performance monitoring system for use with mobile communications devices," filed Apr. 14, 2014.

(Continued)

*Primary Examiner* — George Manuel
(74) *Attorney, Agent, or Firm* — Wilson Sonsini Goodrich & Rosati (57) ABSTRACT

Described herein are apparatuses (e.g., systems, devices) and methods for processing, distributing, and analyzing medical data. In particular, apparatuses and methods for processing and distributing tasks or jobs for completion by a qualified worker or specialist are described. Crowdsourcing data to specialists for interpretation can be accomplished using an auction system to match the specialists with discrete portions of the data. The data can be bundled based on one or more categories or characteristics, and then placed on an auction where the specialists can bid for each bundle by submitting a payment price. The data can be medical data, such as ECG data, imaging data and test data.

26 Claims, 3 Drawing Sheets

(56) References Cited

U.S. PATENT DOCUMENTS

| | | |
|---|---|---|
| 3,768,014 A | 10/1973 | Smith et al. |
| 3,776,228 A | 12/1973 | Semler |
| 3,779,237 A | 12/1973 | Goeltz et al. |
| 3,779,249 A | 12/1973 | Semler |
| 3,782,367 A | 1/1974 | Hochberg et al. |
| 3,805,227 A | 4/1974 | Lester |
| 3,882,277 A | 5/1975 | DePedro et al. |
| 3,885,552 A | 5/1975 | Kennedy |
| 3,898,984 A | 8/1975 | Mandel et al. |
| 3,909,599 A | 9/1975 | Trott, Jr. et al. |
| 4,027,146 A | 5/1977 | Gilmore |
| 4,045,767 A | 8/1977 | Nishihara et al. |
| 4,083,366 A | 4/1978 | Gombrich et al. |
| 4,095,050 A | 6/1978 | Beachem et al. |
| 4,221,223 A | 9/1980 | Linden |
| 4,230,127 A | 10/1980 | Larson |
| 4,231,031 A | 10/1980 | Crowther et al. |
| 4,250,888 A | 2/1981 | Grosskopf |
| 4,281,664 A | 8/1981 | Duggan |
| 4,295,472 A | 10/1981 | Adams |
| 4,312,358 A | 1/1982 | Barney |
| 4,318,130 A | 3/1982 | Heuer |
| 4,364,397 A | 12/1982 | Citron et al. |
| 4,367,752 A | 1/1983 | Jimenez et al. |
| 4,409,984 A | 10/1983 | Dick |
| 4,531,527 A | 7/1985 | Reinhold, Jr. et al. |
| 4,567,883 A | 2/1986 | Langer et al. |
| 4,572,182 A | 2/1986 | Royse |
| 4,580,250 A | 4/1986 | Kago et al. |
| 4,583,553 A | 4/1986 | Shah et al. |
| 4,622,979 A | 11/1986 | Katchis et al. |
| 4,625,730 A | 12/1986 | Fountain et al. |
| 4,630,204 A | 12/1986 | Mortara |
| 4,803,625 A | 2/1989 | Fu et al. |
| 4,889,131 A | 12/1989 | Salem et al. |
| 4,920,489 A | 4/1990 | Hubelbank et al. |
| 4,938,228 A | 7/1990 | Righter et al. |
| 4,938,229 A | 7/1990 | Bergelson et al. |
| 4,958,641 A | 9/1990 | Digby et al. |
| 4,977,899 A | 12/1990 | Digby et al. |
| 4,981,141 A | 1/1991 | Segalowitz |
| 5,012,814 A | 5/1991 | Mills et al. |
| 5,023,906 A | 6/1991 | Novas |
| 5,025,794 A | 6/1991 | Albert et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,136,555 A | 8/1992 | Gardos |
| 5,181,519 A | 1/1993 | Bible |
| 5,191,891 A | 3/1993 | Righter |
| 5,201,321 A | 4/1993 | Fulton |
| 5,218,969 A | 6/1993 | Bredesen et al. |
| 5,226,424 A | 7/1993 | Bible |
| 5,238,001 A | 8/1993 | Gallant et al. |
| D341,659 S | 11/1993 | Homayoun et al. |
| 5,259,387 A | 11/1993 | Depinto |
| 5,289,824 A | 3/1994 | Mills et al. |
| 5,301,679 A | 4/1994 | Taylor |
| 5,304,186 A | 4/1994 | Semler et al. |
| 5,313,953 A | 5/1994 | Yomtov et al. |
| 5,317,269 A | 5/1994 | Mills et al. |
| 5,321,618 A | 6/1994 | Gessman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,351,695 A | 10/1994 | Mills et al. |
| 5,360,005 A | 11/1994 | Wilk |
| 5,365,935 A | 11/1994 | Righter et al. |
| 5,410,587 A | 4/1995 | Grunwell |
| 5,417,222 A | 5/1995 | Dempsey et al. |
| 5,433,736 A | 7/1995 | Nilsson |
| 5,452,356 A | 9/1995 | Albert |
| 5,466,246 A | 11/1995 | Silvian |
| 5,467,773 A | 11/1995 | Bergelson et al. |
| 5,481,255 A | 1/1996 | Albert et al. |
| 5,503,158 A | 4/1996 | Coppock et al. |
| 5,518,001 A | 5/1996 | Snell |
| 5,522,396 A | 6/1996 | Langer et al. |
| 5,539,705 A | 7/1996 | Akerman et al. |
| D372,785 S | 8/1996 | Sabri et al. |
| 5,544,661 A | 8/1996 | Davis et al. |
| 5,551,953 A | 9/1996 | Lattin et al. |
| 5,561,712 A | 10/1996 | Nishihara |
| 5,568,448 A | 10/1996 | Tanigushi et al. |
| 5,579,284 A | 11/1996 | May |
| 5,583,758 A | 12/1996 | McIlroy et al. |
| D377,983 S | 2/1997 | Sabri et al. |
| 5,608,723 A | 3/1997 | Felsenstein |
| 5,613,495 A | 3/1997 | Mills et al. |
| 5,634,468 A | 6/1997 | Platt et al. |
| 5,652,570 A | 7/1997 | Lepkofker |
| 5,661,699 A | 8/1997 | Sutton |
| 5,675,325 A | 10/1997 | Taniguchi et al. |
| 5,678,562 A | 10/1997 | Sellers |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,735,285 A | 4/1998 | Albert et al. |
| 5,742,251 A | 4/1998 | Gerber |
| 5,748,103 A | 5/1998 | Flach et al. |
| 5,764,763 A | 6/1998 | Jensen et al. |
| 5,772,586 A | 6/1998 | Heinonen et al. |
| 5,818,788 A | 10/1998 | Kimura et al. |
| 5,825,718 A | 10/1998 | Ueki et al. |
| 5,827,179 A | 10/1998 | Lichter et al. |
| 5,840,020 A | 11/1998 | Heinonen et al. |
| 5,844,997 A | 12/1998 | Murphy, Jr. |
| 5,861,018 A | 1/1999 | Feierbach |
| 5,873,369 A | 2/1999 | Laniado et al. |
| 5,876,351 A | 3/1999 | Rohde |
| 5,877,675 A | 3/1999 | Rebstock et al. |
| 5,889,730 A | 3/1999 | May |
| 5,908,383 A | 6/1999 | Brynjestad |
| 5,929,761 A | 7/1999 | Van Der Laan et al. |
| 5,941,829 A | 8/1999 | Saltzstein et al. |
| 5,954,640 A | 9/1999 | Szabo |
| D414,870 S | 10/1999 | Saltzstein et al. |
| 5,970,388 A | 10/1999 | Will |
| 5,976,083 A | 11/1999 | Richardson et al. |
| 5,982,297 A | 11/1999 | Welle |
| 5,983,127 A | 11/1999 | Depinto |
| 6,008,703 A | 12/1999 | Perrott et al. |
| 6,014,631 A | 1/2000 | Teagarden et al. |
| 6,024,699 A | 2/2000 | Surwit et al. |
| 6,024,705 A | 2/2000 | Schlager et al. |
| 6,037,704 A | 3/2000 | Welle |
| 6,039,688 A | 3/2000 | Douglas et al. |
| 6,048,319 A | 4/2000 | Hudgins et al. |
| D427,315 S | 6/2000 | Saltzstein et al. |
| 6,072,396 A | 6/2000 | Gaukel |
| 6,083,248 A | 7/2000 | Thompson |
| 6,084,510 A | 7/2000 | Lemelson et al. |
| 6,100,806 A | 8/2000 | Gaukel |
| 6,102,856 A | 8/2000 | Groff et al. |
| 6,126,596 A | 10/2000 | Freedman |
| 6,153,532 A | 11/2000 | Dow et al. |
| 6,159,147 A | 12/2000 | Lichter et al. |
| 6,171,256 B1 | 1/2001 | Joo et al. |
| 6,198,394 B1 | 3/2001 | Jacobsen et al. |
| 6,223,164 B1 | 4/2001 | Seare et al. |
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk |
| 6,343,049 B1 | 1/2002 | Toda |

(56) References Cited

U.S. PATENT DOCUMENTS

| | | |
|---|---|---|
| 6,363,139 B1 | 3/2002 | Zurek et al. |
| 6,364,834 B1 | 4/2002 | Reuss et al. |
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,478,736 B1 | 11/2002 | Mault |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |
| 6,612,985 B2 | 9/2003 | Eiffert et al. |
| 6,616,613 B1 | 9/2003 | Goodman |
| 6,636,761 B2 | 10/2003 | Brodnick |
| 6,685,633 B2 | 2/2004 | Albert et al. |
| 6,717,983 B1 | 4/2004 | Toda |
| 6,790,178 B1 | 9/2004 | Mault et al. |
| 6,804,558 B2 | 10/2004 | Haller et al. |
| 6,820,057 B1 | 11/2004 | Loch et al. |
| 6,845,263 B2 | 1/2005 | Kawaguchi |
| 6,893,396 B2 | 5/2005 | Schulze et al. |
| 6,928,535 B2 | 8/2005 | Yamashita et al. |
| 6,950,681 B2 | 9/2005 | Hofmann |
| 6,970,737 B1 | 11/2005 | Brodnick et al. |
| 6,987,965 B2 | 1/2006 | Ng et al. |
| 7,009,511 B2 | 3/2006 | Mazar et al. |
| 7,018,339 B2 | 3/2006 | Birnbaum et al. |
| 7,020,508 B2 | 3/2006 | Stivoric et al. |
| 7,031,745 B2 | 4/2006 | Shen |
| 7,061,381 B2 | 6/2006 | Forcier et al. |
| 7,103,407 B2 | 9/2006 | Hjelt et al. |
| 7,107,095 B2 | 9/2006 | Manolas |
| 7,108,659 B2 | 9/2006 | Ross et al. |
| 7,136,693 B2 | 11/2006 | Brodnick |
| 7,153,262 B2 | 12/2006 | Stivoric et al. |
| 7,162,294 B2 | 1/2007 | Rowlandson et al. |
| 7,171,166 B2 | 1/2007 | Ng et al. |
| 7,188,151 B2 | 3/2007 | Kumar et al. |
| 7,215,991 B2 | 5/2007 | Besson et al. |
| 7,222,054 B2 | 5/2007 | Geva |
| 7,236,818 B2 | 6/2007 | Mcleod et al. |
| 7,257,448 B2 | 8/2007 | Crowe et al. |
| 7,260,429 B2 | 8/2007 | Siejko et al. |
| 7,261,690 B2 | 8/2007 | Teller et al. |
| 7,285,090 B2 | 10/2007 | Stivoric et al. |
| 7,319,425 B2 | 1/2008 | Fiorenza et al. |
| 7,324,836 B2 | 1/2008 | Steenstra et al. |
| RE40,116 E | 2/2008 | Engstrom |
| 7,349,574 B1 | 3/2008 | Sodini et al. |
| 7,351,207 B2 | 4/2008 | Priemer |
| 7,354,400 B2 | 4/2008 | Asafusa et al. |
| 7,383,297 B1 | 6/2008 | Atsmon et al. |
| 7,415,304 B2 | 8/2008 | Rowlandson et al. |
| 7,444,116 B2 | 10/2008 | Ivanov et al. |
| 7,509,159 B2 | 3/2009 | Xue et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,552,081 B2 * | 6/2009 | Dutta et al. .................... 705/37 |
| 7,596,405 B2 | 9/2009 | Kurzweil et al. |
| 7,603,148 B2 | 10/2009 | Michalak |
| 7,654,148 B2 | 2/2010 | Tomlinson, Jr. et al. |
| 7,657,479 B2 | 2/2010 | Henley |
| 7,668,589 B2 | 2/2010 | Bauer |
| 7,689,437 B1 | 3/2010 | Teller et al. |
| 7,701,895 B2 | 4/2010 | Gehasie et al. |
| 7,733,224 B2 | 6/2010 | Tran |
| 7,742,808 B2 | 6/2010 | Nissilä |
| 7,819,814 B2 | 10/2010 | Gavriely et al. |
| 7,846,104 B2 | 12/2010 | Macquarrie et al. |
| 7,846,106 B2 | 12/2010 | Andrews et al. |
| 7,904,160 B2 | 3/2011 | Brodnick et al. |
| 7,945,064 B2 | 5/2011 | O'Brien, Jr. et al. |
| 7,945,462 B1 * | 5/2011 | Goral ............................. 705/4 |
| 7,946,959 B2 | 5/2011 | Shum et al. |
| 7,955,273 B2 | 6/2011 | Rahe-Meyer |
| 7,983,749 B2 | 7/2011 | Warren |
| 8,019,609 B2 | 9/2011 | Tamir et al. |
| 8,034,006 B2 | 10/2011 | Celik-Butler et al. |
| 8,062,090 B2 | 11/2011 | Atsmon et al. |
| 8,073,707 B2 | 12/2011 | Teller et al. |
| 8,078,136 B2 | 12/2011 | Atsmon et al. |
| 8,078,278 B2 | 12/2011 | Penner |
| 8,109,874 B2 | 2/2012 | Kong et al. |
| 8,126,566 B2 | 2/2012 | Stahmann et al. |
| 8,126,728 B2 | 2/2012 | Dicks et al. |
| 8,130,093 B2 | 3/2012 | Mazar et al. |
| 8,150,750 B2 | 4/2012 | Ray |
| 8,160,276 B2 | 4/2012 | Liao et al. |
| 8,165,677 B2 | 4/2012 | Von Arx et al. |
| 8,224,429 B2 | 7/2012 | Prstojevich et al. |
| 8,265,907 B2 | 9/2012 | Nanikashvili et al. |
| 8,275,635 B2 | 9/2012 | Stivoric et al. |
| 8,282,550 B2 | 10/2012 | Rasdal et al. |
| 8,285,356 B2 | 10/2012 | Bly et al. |
| 8,301,232 B2 | 10/2012 | Albert et al. |
| 8,301,236 B2 | 10/2012 | Baumann et al. |
| 8,315,695 B2 | 11/2012 | Sebelius et al. |
| 8,323,188 B2 | 12/2012 | Tran |
| 8,328,718 B2 | 12/2012 | Tran |
| 8,332,233 B2 | 12/2012 | Ott et al. |
| 8,364,250 B2 | 1/2013 | Moon et al. |
| 8,369,936 B2 | 2/2013 | Farringdon et al. |
| 8,374,688 B2 | 2/2013 | Libbus et al. |
| 8,449,471 B2 | 5/2013 | Tran |
| 8,500,636 B2 | 8/2013 | Tran |
| 8,509,882 B2 | 8/2013 | Albert et al. |
| 8,519,835 B2 | 8/2013 | Dunko |
| 8,525,673 B2 | 9/2013 | Tran |
| 8,543,185 B2 | 9/2013 | Yuen et al. |
| 8,543,351 B2 | 9/2013 | Yuen et al. |
| 8,547,248 B2 | 10/2013 | Zdeblick et al. |
| 8,548,770 B2 | 10/2013 | Yuen et al. |
| 8,583,402 B2 | 11/2013 | Yuen et al. |
| 8,684,900 B2 | 4/2014 | Tran |
| 8,700,137 B2 | 4/2014 | Albert |
| 2001/0025139 A1 | 9/2001 | Pearlman |
| 2001/0027384 A1 | 10/2001 | Schulze et al. |
| 2001/0031998 A1 | 10/2001 | Nelson et al. |
| 2001/0051766 A1 | 12/2001 | Gazdzinski |
| 2002/0016541 A1 | 2/2002 | Glossop |
| 2002/0032386 A1 | 3/2002 | Sackner et al. |
| 2002/0065758 A1 | 5/2002 | Henley |
| 2002/0082665 A1 | 6/2002 | Haller et al. |
| 2002/0111556 A1 | 8/2002 | Wegner |
| 2002/0143576 A1 | 10/2002 | Nolvak et al. |
| 2003/0004425 A1 | 1/2003 | Narimatsu et al. |
| 2003/0093002 A1 | 5/2003 | Kuo |
| 2003/0097153 A1 | 5/2003 | Bardy et al. |
| 2003/0107487 A1 | 6/2003 | Korman et al. |
| 2003/0117987 A1 | 6/2003 | Brebner |
| 2003/0149344 A1 | 8/2003 | Nizan |
| 2003/0193839 A1 | 10/2003 | Singh |
| 2004/0002662 A1 | 1/2004 | Hjelt et al. |
| 2004/0010201 A1 | 1/2004 | Korzinov et al. |
| 2004/0034284 A1 | 2/2004 | Aversano et al. |
| 2004/0044292 A1 | 3/2004 | Yasushi et al. |
| 2004/0059205 A1 | 3/2004 | Carlson et al. |
| 2004/0093331 A1 | 5/2004 | Garner et al. |
| 2004/0117212 A1 | 6/2004 | Kong et al. |
| 2004/0143403 A1 | 7/2004 | Brandon et al. |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0225199 A1 | 11/2004 | Evanyk et al. |
| 2004/0228217 A1 | 11/2004 | Szeto |
| 2004/0236379 A1 | 11/2004 | Bardy et al. |
| 2004/0236819 A1 | 11/2004 | Anati et al. |

(56) References Cited

U.S. PATENT DOCUMENTS

| | | |
|---|---|---|
| 2004/0266407 A1 | 12/2004 | Lee et al. |
| 2004/0266480 A1 | 12/2004 | Hjelt et al. |
| 2005/0014531 A1 | 1/2005 | Findikli |
| 2005/0027207 A1 | 2/2005 | Westbrook et al. |
| 2005/0078533 A1 | 4/2005 | Vyshedskiy et al. |
| 2005/0124864 A1 | 6/2005 | Mack et al. |
| 2005/0234353 A1 | 10/2005 | Xue et al. |
| 2006/0022833 A1 | 2/2006 | Ferguson et al. |
| 2006/0047215 A1 | 3/2006 | Newman et al. |
| 2006/0173259 A1 | 8/2006 | Flaherty et al. |
| 2006/0190045 A1 | 8/2006 | Marcus et al. |
| 2006/0224051 A1 | 10/2006 | Teller et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0032731 A1 | 2/2007 | Lovejoy et al. |
| 2007/0032733 A1 | 2/2007 | Burton |
| 2007/0063850 A1 | 3/2007 | Devaul et al. |
| 2007/0106179 A1 | 5/2007 | Bagha et al. |
| 2007/0156060 A1 | 7/2007 | Cervantes |
| 2007/0254604 A1 | 11/2007 | Kim |
| 2007/0265038 A1 | 11/2007 | Kim |
| 2008/0009759 A1 | 1/2008 | Chetham |
| 2008/0058670 A1 | 3/2008 | Mainini |
| 2008/0097537 A1 | 4/2008 | Duann et al. |
| 2008/0112885 A1 | 5/2008 | Okunev et al. |
| 2008/0146890 A1 | 6/2008 | LeBoeuf et al. |
| 2008/0171945 A1 | 7/2008 | Dotter |
| 2008/0177162 A1 | 7/2008 | Bae et al. |
| 2008/0198872 A1 | 8/2008 | Pierce |
| 2008/0214903 A1 | 9/2008 | Orbach |
| 2008/0221632 A1 | 9/2008 | Bardy et al. |
| 2008/0228045 A1 | 9/2008 | Gao et al. |
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0152598 A1 | 6/2010 | Zhang |
| 2010/0184479 A1 | 7/2010 | Griffin, Jr. |
| 2010/0204758 A1 | 8/2010 | Boon et al. |
| 2010/0208434 A1 | 8/2010 | Kim et al. |
| 2010/0217099 A1 | 8/2010 | LeBoeuf et al. |
| 2010/0217100 A1 | 8/2010 | LeBoeuf et al. |
| 2010/0217144 A1 | 8/2010 | Brian |
| 2010/0217345 A1 | 8/2010 | Wolfe et al. |
| 2010/0256509 A1 | 10/2010 | Kuo et al. |
| 2010/0281261 A1 | 11/2010 | Razzell |
| 2010/0298711 A1 | 11/2010 | Pedersen et al. |
| 2010/0324378 A1 | 12/2010 | Tran et al. |
| 2010/0331631 A1 | 12/2010 | Maclaughlin |
| 2011/0004110 A1 | 1/2011 | Shusterman |
| 2011/0015496 A1 | 1/2011 | Sherman et al. |
| 2011/0035927 A1 | 2/2011 | Griffin et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0152957 A1 | 6/2011 | Shaquer |
| 2011/0160601 A1 | 6/2011 | Wang et al. |
| 2011/0235466 A1 | 9/2011 | Booij et al. |
| 2011/0301439 A1 | 12/2011 | Albert et al. |
| 2011/0319949 A1 | 12/2011 | Bardy et al. |
| 2012/0051187 A1 | 3/2012 | Paulson |
| 2012/0053424 A1 | 3/2012 | Kenalty et al. |
| 2012/0071734 A1 | 3/2012 | Shimuta et al. |
| 2012/0123232 A1 | 5/2012 | Najarian et al. |
| 2012/0123285 A1 | 5/2012 | Zhang |
| 2012/0123891 A1 | 5/2012 | Patel |
| 2012/0127833 A1 | 5/2012 | Ghen et al. |
| 2012/0136264 A1 | 5/2012 | Zhang |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0157802 A1 | 6/2012 | Chou |
| 2012/0158090 A1 | 6/2012 | Chavan et al. |
| 2012/0171963 A1 | 7/2012 | Tsfaty |
| 2012/0179056 A1 | 7/2012 | Moulder et al. |
| 2012/0203124 A1 | 8/2012 | Lim |
| 2012/0221476 A1 | 8/2012 | Candelario |
| 2012/0316413 A1 | 12/2012 | Liu et al. |
| 2013/0030259 A1 | 1/2013 | Thomsen et al. |
| 2013/0046162 A1 | 2/2013 | Baumann et al. |
| 2013/0085364 A1 | 4/2013 | Lu et al. |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0331663 A1 | 12/2013 | Albert et al. |
| 2013/0338460 A1 | 12/2013 | He et al. |
| 2014/0050321 A1 | 2/2014 | Albert et al. |
| 2014/0128758 A1 | 5/2014 | Galloway et al. |
| 2014/0194760 A1 | 7/2014 | Albert |
| 2014/0222097 A1 | 8/2014 | Bardy et al. |
| 2015/0018702 A1 | 1/2015 | Galloway et al. |

FOREIGN PATENT DOCUMENTS

| | | |
|---|---|---|
| CN | 201918016 U | 8/2011 |
| CN | 102347804 A | 2/2012 |
| DE | 2506936 A | 9/1976 |
| DE | 4212670 A1 | 1/1994 |
| EP | 631226 A1 | 12/1994 |
| EP | 0980227 A1 | 2/2000 |
| EP | 1407713 A1 | 4/2004 |
| EP | 1782229 A | 5/2007 |
| EP | 1181888 B1 | 9/2007 |
| EP | 1238633 B1 | 10/2008 |
| EP | 2030565 A1 | 3/2009 |
| EP | 2116183 B1 | 2/2012 |
| FR | 2740426 A1 | 4/1997 |
| GB | 2181554 A | 4/1987 |
| GB | 2408105 A | 5/2005 |
| JP | 59-122032 A | 7/1984 |
| JP | 59-190742 A | 10/1984 |
| JP | 63-072231 A | 4/1988 |
| JP | 63-294044 A | 11/1988 |
| JP | 1-244328 A | 9/1989 |
| JP | 5-167540 A | 7/1993 |
| JP | 6-326669 A | 11/1994 |
| JP | 2002191562 A | 7/2002 |
| JP | 2002-261731 A | 9/2002 |
| JP | 2003-010177 A | 1/2003 |
| JP | 2005-295378 A | 10/2005 |
| JP | 2012-065073 A | 3/2012 |
| MX | 2009011781 A | 5/2011 |
| WO | WO82/00910 A1 | 3/1982 |
| WO | WO88/05282 A1 | 7/1988 |
| WO | WO90/08361 A1 | 7/1990 |
| WO | WO92/06551 A1 | 4/1992 |
| WO | WO97/31437 A1 | 8/1997 |
| WO | WO98/38611 A1 | 9/1998 |
| WO | WO-9838909 A1 | 9/1998 |
| WO | WO-9858338 A2 | 12/1998 |
| WO | WO-9904043 A1 | 1/1999 |
| WO | WO99/44494 A1 | 9/1999 |

(56) References Cited

FOREIGN PATENT DOCUMENTS

| | | |
|---|---|---|
| WO | WO00/41620 A1 | 7/2000 |
| WO | WO01/47597 A2 | 7/2001 |
| WO | WO01/57619 A2 | 8/2001 |
| WO | WO-0233846 A1 | 4/2002 |
| WO | WO02/080762 A1 | 10/2002 |
| WO | WO03/075118 A2 | 9/2003 |
| WO | WO03/094720 A1 | 11/2003 |
| WO | WO2004/037080 A1 | 5/2004 |
| WO | WO-2005124864 A1 | 12/2005 |
| WO | WO2006/001005 A2 | 1/2006 |
| WO | WO-2006021956 A2 | 3/2006 |
| WO | WO2007/014545 A2 | 2/2007 |
| WO | WO2007/088315 A1 | 8/2007 |
| WO | WO2008/005015 A1 | 1/2008 |
| WO | WO 2008/066682 A2 | 6/2008 |
| WO | WO2010/025166 A1 | 3/2010 |
| WO | WO2010/108287 A1 | 9/2010 |
| WO | WO2010/113354 | 10/2010 |
| WO | WO2010/144626 A1 | 12/2010 |
| WO | WO2011/006356 A1 | 1/2011 |
| WO | WO2011/008838 A1 | 1/2011 |
| WO | WO2011/014292 A1 | 2/2011 |
| WO | WO2011/022942 A1 | 3/2011 |
| WO | WO2011/040877 A1 | 4/2011 |
| WO | WO2011/040878 A1 | 4/2011 |
| WO | WO2011/113070 A1 | 9/2011 |
| WO | WO2011/137375 A2 | 11/2011 |
| WO | WO2012/046158 A1 | 4/2012 |
| WO | WO2012/108895 A1 | 8/2012 |
| WO | WO2012/129413 A1 | 9/2012 |
| WO | WO2012/160550 A1 | 11/2012 |
| WO | WO2013/036307 A1 | 3/2013 |
| WO | WO2013/066642 A1 | 5/2013 |
| WO | WO2013/093690 A1 | 6/2013 |
| WO | WO2013/122788 A1 | 8/2013 |
| WO | WO2013/138500 A1 | 9/2013 |
| WO | WO2013/155196 A2 | 10/2013 |
| WO | WO2013/192166 A1 | 12/2013 |

OTHER PUBLICATIONS

Adidas miCoach Pacer Review: Like Nike+, Only Better; printed from website http://gizmodo.com/5479456/adidas on Mar. 4, 2010; 5 pgs.

Australian Design Awards; Heartplus Micro; printed from website http://www.designawards.com/au on Apr. 12, 2002; 6 pgs.

Bajaj, M.D.; Event Recording in Ambulatory Patients with Syncopal Events; University of Kansas; Wichita, Kansas; (no date); pp. 15-18; printed on or before Apr. 14, 2010.

Bluetooth; Headset Profile (HSP); printed from website http://bluetooth.com/English/Technology/Works/Pates/HSP.aspx, printed May 12, 2010; 1 pg.

Bramanti et al., Multichannel telemetric system for biomedical signals via switched telephone lines; Medical and Biological Engineering and Computing, Sep. 1982, vol. 20, No. 5, pp. 653-656.

Burke, A Micropower Dry—Electrode ECG Preamplifier; IEEE Transactions on Biomedical Engineering, Feb. 2000, vol. 47, No. 2, pp. 155-162.

Card Guard; CG-6108 ACT Ambulatory Cardiac Telemetry Brochure; Card Guard, The Telemedicine Company: Switzerland; (year of publication is sufficiently earlier than the effective U.S. filing date and any foreign priority date) 2006; 2 pgs.

Cardiocomm Solutions; GEMS Air (PC based ECG management); printed from website http://www.cardiocommsolutions/com on Mar. 19, 2010; 1 pg.

Charuvastra; Transtelephonic Cardiac Event Recording for Arrhythmia Surveillance; printed from website http://tchin.org/resource_room/c_art on Mar. 26, 2010; 2 pgs.

Cheng, Allen C.; Real-Time Cardiovascular Diseases Detection on a Smartphone; printed Apr. 14, 2010.

Company-Bosch et al.; ECG Front-End Design is Simplified with MicroConverter; Analog Dialogue; Nov. 2003; vol. 37(11); pp. 1-5.

Creative; PC-80B Portable ECG Monitor w/sd card extension slot; printed from website www.amazon.com/Portable-Monitor-extension-leather-shipping/dp/B001OjWKUE on Feb. 4, 2010; 3 pgs.

Deveau, Health care eyes smart phones to heal ills (posted Sep. 15, 2009); printed from website http://www.theQiobeandmail.com on Sep. 17, 2009, 4 pages.

Dinh; Heart Activity Monitoring on Smartphone; IPCBEE—Int Conf Biomedical Eng and Technol; 11:45-49; Jun. 17-19, 2011.

Dobrev, et al.; Bootstrapped two-electrode biosignal amplifier; Med Biol Eng Comput; vol. 46(6); Jun. 2008, pp. 613-619.

Dolan; Qualcomm launches ECG smartphone program in China; Sep. 8, 2011; 11 pgs.; retrieved Mar. 19, 2014 from the internet (http://mobihealthnews.com/13092/qualcomm-launches-ecg-smartphone-program-in-china/).

Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http://hypertextbook.com/facts/2003/ChrisDAmbrose.shtml).

Favorite Plus; Handheld Easy ECG Monitor; (Product ID: FP180); printed from website www. favoriteplus.com/easy-ecg-handheld-monitor-fp180 on Feb. 4, 2010; 2 pgs.

Favorite Plus; Handheld ECG Monitor—Handheld EKG Monitor at Favoriteplus.com (Products: FP180, FP-RMH and FP-ICH); printed from website www.favoriteplus.com/handheld-ecg-ekg-monitor.php on Feb. 4, 2010; 3 pgs.

Favorite Plus; Handheld EKG Monitor InstantCheck; (Product ID: FP-ICH); printed from website http://www. favoriteplus.com/instanchcheck-hand held-ecg-ekg-monitor on Feb. 4, 2010; 2 pgs.

Ferrick, M.D., Holter Monitoring and Cardiac Event Recording in Assessing Symptomatic Patients; Albert Einstein College of Medicine; Bronx, New York; (no date); pp. 11-14; printed on or before Apr. 14, 2010.

FREE2MOVE; Vitaphone 2300; www.free2move.us/News/NewsVitaphone240105.htm; printed May 12, 2010; 2 pgs.

Fulford-Jones, et al., A Portable, Low-Power, Wireless Two-Lead EKG System; Proc. of the 26th Ann. Int. Conf. IEEE EMBS; San Francisco, CA, USA; Sep. 1-5, 2004, pp. 2141-2144.

Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No. IA02-1; May 11, 2012.

GBI Portal; Qualcomm's wireless reach mHealth project to improve cardiovascular disease in resource scarce China; Feb. 17, 2012; 7 pgs.; retrieved Mar. 19, 2014 from the internet (http://www.integrallc.com/2012/02/17/qualcomms-wireless-reach-mhealth-project-to-improve-cardiovascular-disease-in-resource-scarce-china/).

Gillette, M.D.; Diagnosis of Pediatric Arrhythmias with Event Recording; Medical University of South Carolina; Charleston, South Carolina; (no date); pp. 25-32; printed on or before Apr. 14, 2010.

Grier, James W.; How to use 1-lead ECG recorders to obtain 12-lead resting ECGs and exercise ("stress") ECGs; printed from website http://www.ndsu.edu/pubweb/grier on Jun. 7, 2010; 13 pgs.

Hannaford, Kat; How to Turn Your iPhone Into a Laser, Fan or Flashlight; printed from website http://m.gizmodo.com/5534904; printed Feb. 3, 2011.

Hayes, M.D., Approaches to Diagnosing Transient Arrhythmias—An Overview; Mayo Clinic; Rochester, Minnesota; (no date); pp. 7-10; printed on or before Apr. 14, 2010.

Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.org/hlasurvival1.html).

Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/October2007/ClincalHuangOctober2007.aspx).

IMEC News; IMEC extends flexible ECG patch to enable arrhythmia detection; printed from website http://www2.imec.be/imec on Aug. 18, 2009; 1 pg.

(56) References Cited

OTHER PUBLICATIONS

Instromedix; Cardiac Event Recording FAQs; Instromedix: A Card Guard Company, San Diego, CA; printed from website www.instromedix.com/pdf/products/cardiac; printed on or before Apr. 14, 2010.
Instromedix; The Arrhythmia Monitoring System; King of Hearts Express AF Recorder Brochure; from Instromedix; A CardGuard Company; Rosemont IL; (year of publication is sufficiently earlier than the effective U.S. filing date and any foreign priority date) 2004; 3 pgs.
iRHYTHM; Zio(TM) Patch; printed from website http://www.irhythmtech.com/zio-solution/zio-pach/, printed Apr. 12, 2010.
Jenkins II, W.; Time/Frequency Relationships for an FFT-Based Acoustic Modem; Naval Postgraduate School; pp. 1-102; Sep. 2010 (http://edocs.nps.edu/npspubs/scholarly/theses/2010/Sep/10Sep_Jenkins.pdf) printed Oct. 2, 2013.
Kim, et al., Detection of Atrial Fibrillation Episodes using Multiple Heart Rate Variability Features in Different Time Periods; Conf Proc IEEE Eng Med Biol Soc.; EMBS; 30th Ann. Int. Conf.; Aug. 20-25, 2008, 5482-5485.
Koerner; The Author's Metrics; Wired Magazine Article; New York, NY; Jul. 2009; pp. 93-126.
Kumparak, Greg; Visa officially announces their case that turns your iPhone into a credit card (and we've got pics!); May 17, 2010; www.mobilecrunch.com; printed Feb. 3, 2011.
Lau et al. Validation of an iPhone ECG application suitable for community screening for silent atrial fibrillation—A novel way to prevent stroke (Presentation Abstract 16810); American Heart Association 2012 Scientific Sessions and Resuscitation Science Symposium; 126(1); Nov. 20, 2012.
Leijdekkers et al., Trial Results of a Novel Cardiac Rhythm Management System using Smart Phones and Wireless ECG Sensors; Proc. of the 7th Int. Conf. on Smart homes and health Telematics., Tours, France; Jul. 1-3, 2009; 8 pgs.
Levkov et al., Removal of power-line interference from the ECG: a review of the subtraction procedure; BioMedical Engineering Online; 4:50; Aug. 23, 2005; 18 pgs.; (printed from website http://www.biomedical-engineeringonline.com/content/4/1/50).
Lowres, et al. Screening Education and Recognition in Community pHarmacies of Atrial Fibrillation to prevent stroke in an ambulant population aged >=65 years (SEARCH-AF stroke prevention study): a cross-sectional study protocol. BMJ Open. Jun. 25, 2012; 2(3); pii: e001355. doi: 10.1136/bmjopen-2012-001355.
M Med Choice; (company information page) Beijing Choice Electronic Technology Co., Ltd.; printed from website http://www.choicemmed.com/1xwm .asp; printed Dec. 28, 2009; 1 page.
M Med Choice; Handheld ECG Monitor Brochure; MD100 Products; Beijing Choice Electronic Technology Co. Ltd.; 6 pgs; published on or before Apr. 14, 2010.
M Med Choice; Handheld ECG Monitor MD100A1; printed from website http://www.choicemmed.com/productshow.asp on Dec. 28, 2009; 2 pgs.
M Med Choice; Handheld ECG Monitor MD100B; printed from website http://www.choicemmed.com/productshow.asp on Dec. 28, 2009; 2 pgs.
MacFarlane et al.; Resting 12-lead ECG electrode placement and associated problems; SCST Update 1995; 15 pgs.; printed Feb. 18, 2014 from www.scst.org.uk/resources/RESTING_12.pdf? (year of pub. sufficiently earlier than effective US filing date and any foreign priority date).
Mauvila: Mauvila ECG Tutorial; Basic ECG Interpretation Tutorial; Sections 1-12; 2004; printed from website http://mauvila.com/ECG/ecg.htm on Mar. 26, 2010; 57 pgs.
MedGadget; Zio(TM) Patch Wins Medical Design Award; MedGadget internet journal of emerging medical technologies; printed from website http://medgadget.com/archives/2010/04/zio patch wins medial desian award 1.html on Apr. 12, 2010; 1 pg.
MiCardioMobile: Remote Wireless Cardiac Rehabilitation Monitoring printed from website; http://alivetec.cable.nu/cardiomobile; 1 page; printed Apr. 14, 2010.
Mobility Mind; Use your Treo 650 as a portable ECG monitoring device; Mobility Mind; Sep. 14, 2005, printed from website http://www.treotoday.net/2005/09/14/use-your-treo-650-as-a-portable-ecg-monitoring-device/ (accessed Mar. 26, 2010); 1 pg.
Modem Protocols Explained; ftp://kermit.columbia.edu/kermit/cu/protocol.html; 5 pgs.; printed Oct. 2, 2013.
Modem Tutorial; http://www.lsu.edu/OCS/its/unix/tutorial/ModemTutorial/ModemTutorial.html; 2 pgs.; printed Oct. 2, 2013.
Muench, Frederick PhD; HRV: The Manufacturers and Vendors Speak; The portable StressEraser Heart Rate Variability Biofeedback Device: Background and Research; Biofeedback; vol. 36, Iss. 1; pp. 35-39; Spring 2008.
Murph; RedEye mini converts iPhone, iPad or iPod touch into IR-beaming universal remote; printed from website http://www.engadget.com/2010/03/02/redeye on Mar. 2, 2010; 2 pgs.
Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).
Neuroreille; Audiometry; web version as of Oct. 14, 2008; 1 pg.; printed Jun. 6, 2012 (http://www.neuroreille.com/promenade/english/audiometry/audiometry.htm).
Omron; Omron Portable ECG EKG Handheld HCG-801 Monitor; printed from website http://www.amazon.com/Omron-Portable-Handheld-HCG-801-Monitor/dp/B0019WH3EO on Feb. 24, 2010; 4 pgs.
Omron; Omron Portable ECG Monitor; printed from website http://www.target.com/gp/detail.html on Mar. 26, 2010; 1 pg.
Oresko, et al., Detecting Cardiovascular Diseases via Real-Time Electrocardiogram Processing on a Smartphone; 2009 Workshop on Biomedicine in Computing: Systems, Architectures, and Circuits (BiC); Austin, TX; Jun. 2009; pp. 13-16.
Perez, Sarah; No NFC? No Problem; New Startup Zoosh Provides Workaround Technology (Jun. 20, 2011); printed on or before Jun. 27, 2011 from website; 2 pgs.; (http://www.readwriteweb.com/archives).
Prystowsky, M.D., Chairmans Introduction; Duke University Medical Center; Indianapolis, Indiana; pp. 5-6; printed on or before Apr. 14, 2010.
Prystowsky, M.D., Chairmans Summary; Duke University Medical Center; Indianapolis Indiana; (no date); pp. 39-40; printed on or before Apr. 14, 2010.
Prystowsky, M.D., The Clinical Application, Diagnostic Yield and Cost Considerations of Cardiac Event Recorders; Duke University Medical Center; Indianapolis Indiana; (no date); pp. 19-23. printed on or before Apr. 14, 2010.
Puurtinen, et al., Best Electrode Locations for a Small Bipolar ECG Device: Signal Strength Analysis of Clinical Data, Annals of Biomedical Engineering, vol. 37, No. 2, Feb. 2009; pp. 331-336.
Raju; Heart-Rate and EKG Monitor Using the MSP430FG439 (Application Report); Texas Instruments; SLAA280—Oct. 2005—(Revised Sep. 2007); 11 pgs.
Read-My-Heart; ECG Machine Handheld Read My Heart; (Product Item No. HH-3413); printed from website http://www.helioliving.com/ECG-Machine-Handheld-ReadMyHeart on Feb. 4, 2010; 1 pg.
Read-My-Heart; ReadMyHeart Personal Handheld ECG Monitor with Free Illustrator Book & Free Electrodes V2.2; printed from website http://www.amazon.com/Readmyheart-Personal-Handheld-illustrator-Electrodes/dp/B0010AN63W on Mar. 26, 2010; 1 pg.
Ricker; Square payment dongle demoed for iPhone toting hippies and you (video); printed from website http://www.engadget.com/2010/01/18/square-payment on Jan. 18, 2010; 6 pgs.
Rockwood; Interviews: The Networked Body Magazine Article from Fast Talk Magazine; Jul. 2009; pp. 19-26.
Salahuddin, et al., Ultra Short Term Analysis of Heart Rate Variability using Normal Sinus Rhythm and Atrial Fibrillation ECG Data; e-Health Networking, App. and Services; 9th Int. Conf.; IEEE; Taipei, TW; pp. 240-243; Jun. 19-22, 2007.
Saxon, et al. iPhone rhythm strip—the implications of wireless and ubiquitous heart rate monitoring. JACC; 59(13): E726; Mar. 2012.

(56) References Cited

OTHER PUBLICATIONS

Semler, M.D.; The Future of Cardiac Event Monitoring; St. Vincent Hospital and Medical Center; Portland, Oregon; (no date); pp. 33-37; printed on or before Apr. 14, 2010.
SFO Medical; Choice Portable Handheld ECG EKG Monitor; printed from website http://www.amazon.com/Choice-Portable-Handheld-ECG-Monitor/dp/B001Q74VOM on Mar. 26, 2010; 1 page.
Shenzen New Element Med. Equipment; Wireless ECG Monitoring System; printed from website http://www.alibaba.com/product-gs/248168581/Wireless ECG Monitoring system.html. on Mar. 26, 2010.
Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.
Smith; Smartphone may keep the cardiologist away; The Independent; Mar. 5, 2010; printed from website http://www.independent.co.uk/life-style/health-and-families/health-news/smartphone-may-keep-the-cardiologist-away-1916652.html on Mar. 26, 2010.
Stevens, Tim; Apple's Seamlessly Embedded Heart Rate Monitor could turn theiPhone into a new-age mood ring (posted May 6, 2010); printed from website www.engadget.com on May 6, 2010; 3 pgs.
TALEB Medical; Observer Hand-held ECG Monitor MD100B; printed on or before Apr. 14, 2010.
Tei, et al., New index of combined systolic and diastolic myocardial performance: a simple and reproducible measure of cardiac function—a study in normals and dilated cardiomyopathy; J Cardiol.; 26(6):357-366; Dec. 1995.
Texas Instruments; Information for Medical Applications, Biophysical Monitoring—Electrocardiogram (ECG) Front End; Apr. 2004, pp. 17-18.
Tschida (posted by); Power A's New Case Turns Your iPhone Into a Universal Remote; printed from website http://appadvice.com/appnn on Mar. 1, 2010; 2 pgs.
Vanhemert, Kyle; XWave Headset Lets You Control iPhone Apps With Your Brain; Sep. 8, 2010; printed from website http://gizmodo.com; printed Sep. 8, 2010.
Vitaphone; Telemedicine since 1999: Modern health management is our special subject; 3 pgs; retrieved Mar. 19, 2014 from the internet (http://www.vitaphone.de/en/company/history-of-vitaphone/).
Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).
Wikipedia; Aliasing; web version as of Apr. 3, 2011; 5 pgs.; printed Jun. 6, 2012 (http://liveweb.archive.org/http://en.wikipedia.org/w/index.php?title=Aliasing&oldid=422141882).
Wikipedia; Hearing Range; web version as of Feb. 6, 2010; 5 pgs.; printed Jun. 6, 2012 (http://web.archive.org/web/20100206213741/http://en.wikipedia.org/wiki/Hearing_range).
Wikipedia; Pulse oximetry; printed from website httg://en.wikipedia.org on May 10, 2010, 4 pages.
Wisneski, C.; Ultrasonic Local Area Communication; http://alumni.media.mit.edu/~wiz/ultracom.html; 2 pgs.; printed Oct. 2, 2013.
Woodward et al.; Bio-Potential-To-Frequency Converter/Modulator; Electronic Design; Aug. 9, 1999; p. 117.
Ziegler, Chris; EPI Life phone sports ECG function, can let doctors know if you're not gonna make it; printed from website http://www.engadget.com/2010/06/16/epi-life-phonesports on Jun. 17, 2010; 4 pgs.
Hickey, et al. Detection of Recurrent Atrial Fibrillation Utilizing Novel Technology. Journal of Atrial Fibrillation. Dec. 2013-Jan. 2014; 6(4):50-52.
Lau, et al. iPhone ECG application for community screening to detect silent atrial fibrillation: A novel technology to prevent stroke. Int J Cardiol. Apr. 30, 2013;165(1):193-4.
Lau, et al. Performance of an Automated iPhone ECG Algorithm to Diagnose Atrial Fibrillation in a Community AF Screening Program (Search-AF). Heart, Lung and Circulation. 2013; 22(1): S205; 2013 (Abstracts for the Cardiac Society of Australia and New Zealand Annual Scientific Meeting and the International Society for Heart Research Australasian Section Ann. Scientific Meeting, Aug. 8-11, 2013, Gold Coast).
Saxon. Ubiquitous Wireless ECG Recording: A Powerful Tool Physicians Should Embrace. J Cardiovasc Electrophysiol. 24(4): pp. 480-483; Apr. 2013.
Albert et al.; U.S. Appl. No. 14/149,242 entitled "Methods and systems for electrode placement," filed Jan. 7, 2014.
Dolan. FDA promises regulatory guidance this year. Mobihealthnews. Mar. 17, 2011. (http://mobihealthnews.com/10495/fda-promises-regulatory-guidance-this-year/).
Dower, et al. Time-selective filtering for computerized electrocardiography. Computers in Cardiology. Sep. 1979; 267-270.
Fausti-Flora, et al. Data Critical's RhythmStat XL Technology Receives FDA Clearance Bringing a Revolutionary Wireless Solution to the Telemedicine Marketplace. Business Wire. Dec. 11, 1997.
Ferrick, M.D.; Holter Monitoring and cardiac Event Recording in Assessing Symptomatic Patients; Albert Einstein College of Medicine; Bronx, New York; (no date) pp. 11-14. printed on or before Apr. 14, 2010.
Haberman et al. Wireless smart phone equipped ECG enables large scle screening in diverse populations. Unpublished abstract. 2 pages.
Hartmann, et al. ECG Front-End Design is Simplified with MicroConverter Analog Dialogue, Nov. 2003, vol. 37, pp. 1-5.
PCT/US2013/069290 International Search Report and Written Opinion dated Feb. 24, 2014.
PCT/US2014/030780 International Search Report Dated Aug. 18, 2014.
Lowres et al., Feasibility and cost effectiveness of stroke prevention through community screening for atrial fibrillation using iPhone ECG in pharmacies. Thrombosis and Haemostasis, 111.6, 2014, 2 pages.
McManus et al. A novel application for the detection of an irregular pulse using an iPhone 4S in patients with atrial fibrillation. Heart Rhythm, 10:315-319 (2013).
Ochs. The Wello smartphone case puts health data in the palm of your hand. Mar. 6, 2014. TechHive blog. http://www.techhive.com/article/2105322/the-wello-smartphone-case-puts-health-data-in-the-palm-of-your-hand.html.
U.S. Appl. No. 14/076,076 Office Action Dated Jan. 29, 2015.
Rohan. How to Save Lives with CE: Data Critical Corp's RhythmStat XLS Interview with developers David Albert, MD and Landgrave Smith, Ph.D. 1999.(http://www.bitcave.com/savelive.pdf).
Telecompaper. Data Critical Launches RhythmStat XL Medical System. Jan. 8, 1998. (http://www.telecompaper.com/news/data-critical-launches-rhythmstat-xl-medical-system-- 126725.
WELLO by Azoi inc. 2014. https://azoi.com/ (accessed Jul. 29, 2015).

* cited by examiner

SYSTEMS AND METHODS FOR PROCESSING AND ANALYZING MEDICAL DATA

CROSS REFERENCE TO RELATED APPLICATIONS

This patent application claims priority to U.S. Provisional Patent Application No. 61/800,879, filed Mar. 15, 2013 (titled "SYSTEMS AND METHODS FOR PROCESSING AND ANALYZING MEDICAL DATA"). This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The systems, devices and methods described herein relate to the processing and analyzing of medical data.

BACKGROUND

Ambulatory electrocardiogram (ECG) monitoring can be useful to detect transient cardiac abnormalities or problems that are difficult to detect using a standard ECG recording device. One type of device used for ambulatory ECG monitoring is an event recorder which can be worn or carried by the user to record ECG data for typically a relatively short duration. The event recorder can continuously record ECG data while only storing the most recent ECG on a rolling basis, and/or the event recorder can be activated manually by the user to record ECG data. Conventionally, the ECG data from the event recorders are sent to a receiving center or the user's physician where the ECG data can be interpreted by a specialist.

However, the ease of use of such ambulatory ECG monitors, as well as the widespread availability of such device for operation by patients themselves, a tremendous amount of patient-specific medical data is being generated. Although automated solutions to review and analysis of this data have been proposed and are being developed (see, e.g., U.S. patent application Ser. No. 14/076,076, filed Nov. 8, 2013 and titled "ELECTROCARDIOGRAM SIGNAL DETECTION"), such techniques are most valuable to pre-screen or triage the medical information, some or all of which may still have to be reviewed by trained medical technicians and/or physicians.

Review of other medical data, such as medical imaging data including x-rays, MRIs, ultrasound, CT scans, PET scans and the like, is traditionally interpreted by one of the patient's medical providers. Alternatively, medical data is increasingly outsourced to specialists for interpretation. These outsourcing specialists can be located overseas and can belong to an outsourcing center that provides low cost medical data interpretation services. U.S. Pat. No. 7,657,479 to Henley ("Method and System for Provision and Acquisition of Medical Services and Products") describes an online matching method and system for verifying medical service provides and allowing verified providers to bid on personal medical services. See also, U.S. Pat. No. 8,150,750 to Ray titled "Systems and Method for Managing Expert Content". U.S. Publication No. 2012/0123891 to Neilesh Patel titled "Professionally-Qualified Bidding System for a User Seeking Professional Services" also describes a systems and method related to using auction systems to match medical providers with users seeking medical services.

However, such systems as those provided above do not adequately pre-sort or triage the information to be reviewed. Further, such systems are adapted more for small, discrete amounts of information (e.g., single patient consultations, etc.), and do not work well at handling the large amounts of information that may be generated by ambulatory ECG systems and the like. What is needed are systems and methods capable of pre-screening, organizing and matching (triaging) such medical information, and particularly ECG information, before or as part of the auctioning process. Described herein are systems and methods related triaging and bundling medical information (e.g., ECGs) that may address the shortcomings of existing and proposed systems.

SUMMARY OF THE DISCLOSURE

The systems, devices and methods described herein relate to the processing and analyzing of medical data, and in particular, relate to crowdsourcing the medical data to qualified specialists for interpretation or analysis by presorting or categorizing the medical data (e.g., electrocardiograms or ECGs) into groups (or bundles) that share one or more common characteristics. Grouping otherwise similar data, such as ECGs, into groups based on one or more similar characteristics dramatically increases the efficiency and rate at which the medical data may be analyzed, and also increases the appeal of the analysis process to potential reviewers. The sorted groups may be size limited (e.g., to a predetermined number of ECG traces, or a total time of ECG traces). Thus, there may be groups that are identical in their shared characteristic(s), though they include different user data.

In particular, with respect to ECG data, the ECG traces included as part of the ECG data may be pre-processed, e.g., to filter, annotate, truncate, or the like. For example, an automated process of pre-screening and/or filtering the ECG signals may be performed. This process may be performed by the recording device (e.g., locally) and/or by the processor receiving the data.

For example, a method for analyzing ECG data may include receiving ECG data from a plurality of users in a server having a processor and memory; categorizing, using the processor, the ECG data into groups based on extracted ECG features; listing the categorized ECG groups by category on an online auction house; receiving bids for the listed ECG groups from registered specialists; determining, using the processor, which specialist won a bid for a group from the listed ECG groups; and providing the specialist that won the bid for the group with access to the ECGs within the group. The method may also include receiving interpreted ECG data from the specialist for the ECGs within the group.

In general, the ECG data may include ECG traces, including raw ECG traces, filtered ECG traces, or a combination of the two. ECG traces may be truncated or annotated. ECG features may be extracted using the processor, and/or the processor may receive ECG data and extracted ECG features from the plurality of users.

Categorizing may include categorizing the ECG data into groups based on extracted ECG features. Any appropriate ECG features, e.g., feature of the actual ECG trace, and/or feature of the manner, time, location or patent when the ECG was taken. For example, ECG features may include location information about where the ECG was taken (geographical location), or the location on the body from where the ECG was taken (chest, etc.). Extracted ECG features may include user annotations, including annotations indicating user status (resting, active), user age, gender, etc. Such information is particularly useful in combination with other ECG features, particularly quantitative features extracted from the ECG trace(s). Extracted ECG features may also include one or more of: amplitude, polarity, duration, or shape of the P, Q, R, S and T waves and QRS complex; ratios and amplitude differences between P, Q, R, S and T waves, or QRS complex; beat to beat variability between P, Q, R, S and T waves, or QRS complex; P-R interval; QRS interval; Q-T interval; S-T interval; P-R segment; S-T segment; and beat to beat frequency.

Any of the methods and apparatuses (including software, hardware and firmware) described herein may also determine an accuracy rating for a particular medical specialist. If the medical specialist is below a predetermined accuracy threshold, then the group analyzed by the medical specialist can be re-introduced for analysis by another medial specialist. A predetermined threshold for accuracy may be based on a percentage accuracy. For example, accuracy may be assessed by inserting at least one reference ECG (e.g., a known/already analyzed ECG) in the ECG groups and comparing the analysis of the reference ECG by the medical specialist that reviews a particular group including the reference ECG with the known analysis of the reference ECG. The lower percent identity between the medical specialist that analyzed the group and the known analysis, the more likely that the group will be placed back in for re-bidding an re-analysis (e.g., less than 80% identical, less than 70% identical, less than 60% identical, less than 50% identical, less than 40% identical, etc.). In some variations the comparison is yes/no. For example, if there is a match between the analysis by the medical specialist (100% match) or if there is no match (e.g., 0% match). For example, at least one reference ECG may be inserted in some (or all) of the ECG groups. An accuracy may be determined for the received interpreted ECG data based on the specialists' interpretation of the reference ECG. For example, at least one reference ECG may be inserted in each ECG group and an accuracy of the received interpreted ECG data may be determined based on the specialists' interpretation of the reference ECG; if the accuracy is below a predetermined threshold, the group of ECGs on the online auction house may be re-listed. The accuracy of a medical specialist may also be examined by duplicating a user's ECG data between two or more groups and comparing the resulting analysis. By comparing the two analyses of the same ECG in different groups (e.g., analyzed by two different medical specialists or the same medical specialist), an estimate of the accuracy, or at least consistency, may be determined. If the two or more analysis do not match, the two or more groups of ECGs may be re-listed on the online auction house (e.g., when the agreement between the interpreted ECG data for the duplicated ECG data is below a predetermined threshold).

Any of the methods or system may also be adapted to notify a user that the user's ECG data has been interpreted. In addition or alternatively, the user may be provided with a list of local specialists based on location information provided with ECG data from the user. In method or system may also schedule an appointment for a user (e.g., using the processor) with a local specialist. In some variation, scheduling may be provided particularly if the analysis reveals an anomaly or indicates further analysis or monitoring of the subject would be beneficial.

Apparatuses, including devices having a processor that is configured (e.g., by running software or the like) to operate as described to analyze medical data. For example, described herein are non-transitory computer-readable storage media storing instructions capable of being executed by a processor, that when executed by the processor causes the processor to: receive ECG data from a plurality of ECG recording devices; categorize the ECG data into a plurality of groups based on extracted ECG features; list the ECG groups by category on an online auction house; receive bids for the listed ECG groups from registered specialists; determine which specialist won a bid for a group from the listed ECG groups; and provide the specialist that won the bid for the group with access to the ECGs within the group.

The set of instructions, when executed by the processor, may causes the processor perform any of the steps described. For example, the set of instructions, when executed by the processor, may further cause the processor to determine an accuracy for the specialist.

Thus, in general a method for analyzing ECG data is provided. The method may include recording ECG data from a plurality of users using ECG recording devices; transmitting the ECG data to a server having a processor and memory; extracting, using the processor, a plurality of ECG features from the ECG data; categorizing, using the processor, the ECG data into at least two categories based on the extracted ECG features; bundling, using the processor, the categorized ECG data into ECG bundles; listing the ECG bundles on an online auction house; receiving at the online auction house bids on the listed ECG bundles from registered specialists; determining, using the processor, which bids are winning bids; providing specialists with the winning bids online access to the ECG bundles; and receiving at the server interpreted ECG data from the specialists.

The method may further include attaching location information to the ECG data. In some embodiments, the location information is provided by a GPS transceiver. In some embodiments, the location information is provided by the user. The method may include compiling, using the processor, a list of local specialists based on the attached location information and providing the user with the list. The method may further include scheduling an appointment, using the processor, with one of the local specialists provided to the user.

In general, the method may include annotating (e.g., attaching user notes to) the ECG data, wherein the user notes are taken contemporaneously with the recording of the ECG data. The user notes may comprise at least one of user symptoms and user activities.

As mentioned, the method further includes notifying users that the ECG data has been interpreted. In any of these variations, the methods or systems may also update the user's electronic health or medical record and/or storing the both the ECG data and the interpreted ECG data in a database.

A system for acquiring and analyzing ECG data may include a plurality of ECG recording devices that generate ECG data; and a server programmed to: receive ECG data from the plurality of ECG recording devices; extract a plurality of ECG features from the ECG data; categorize the ECG data into at least two categories based on the extracted ECG features; and bundle the categorized ECG data into ECG bundles; list the ECG bundles on an online auction house; receive bids on the listed ECG bundles from registered specialists; determine which bids are winning bids; provide specialists with the winning bids online access to the ECG bundles; and receive interpreted ECG data from the specialists. The ECG recording device may include a smartphone. The ECG recording device may include a GPS transceiver.

In general, the methods and systems described herein may provide for the use of bidding by medical specialists on groups of medical data, and particularly ECG data. Such methods and systems may take advantage of crowd-sourcing for ECG interpretation and management, and may vet or select the medical specialist. Any of the methods described herein may include a method providing an interpretation of cardiac data of a user, and may include some or all of the steps of: receiving, at a remote server, cardiac data of a plurality of users and a plurality of bids from a plurality of medical specialists; selecting, with the remote server, a medical specialist subgroup of the plurality of medical specialists; providing the medical specialist subgroup access to the received cardiac data; and receiving, at the remote server, an interpretation of the received cardiac data generated from the subset of the plurality of medical professionals. The presentation of the groups of medical data (ECGs) may be offered only to a sub-set of the specialists.

Ultimately, the selection of the medical specialist subgroup may be determined by winning bid from the received plurality of bids, the winning bid being associated with the medical specialist subset. Pre-screening of the set of medical specialists may include preselecting based on one or more of price, availability, location, language fluency, experience, or certification. In some variations the selection among bids from medical specialists that have been provided a listing of groups of ECGs may be made by ranking all or a subset of: price, availability, location, language fluency, experience, response time, prior accuracy, or certification.

The measurement of the ECG information may require a prescription. Thus any of the methods described herein may include or be methods of providing an interpreted cardiac parameter to a subject that include one or more of the steps of: receiving a cardiac parameter of a subject from a cardiac parameter sensing system prescribed to the subject by a prescribing physician; providing a plurality of medical professionals access to the cardiac parameter; and sending an interpretation of the sensed cardiac parameter to the subject, wherein the interpretation is generated by one or more medical professionals of the plurality of medical professionals other than the prescribing physician.

In general, the cardiac parameter sensing system may include a smartphone, tablet computer, or wearable computer and a sensor in communication with the smartphone, tablet computer, or wearable computer. Thus, a cardiac parameter may be received from a smartphone, tablet computer, or wearable computer, and the method or system may also include sending the interpretation to the smartphone, tablet computer, or wearable computer. The smartphone, tablet computer, or wearable computer may be configured to receive the sent interpretation and display the interpretation in response. For example, displayed through a user interface of the smartphone, tablet computer, or wearable computer.

Any of the methods and systems described herein may include displaying the results of the communication with the remote server, including displaying of results, locally to the user. For example, any of these methods or systems may include or be adapted to perform any of the steps including: receiving, at a remote server, cardiac data of a user transmitted from a local computing device removably coupled to a protective case comprising a sensor configured for sensing the cardiac data and transmitting the sensed cardiac data to the local computing device; providing a medical specialist access to the received cardiac data at the remote server; receiving, at the server, a medical specialist interpretation of the accessed cardiac data; and sending the received cardiac data interpretation from the remote server to the local computing device for display on a display of the local computing device. Thus, for example, received cardiac data of the user may include location information from the local computing device.

As mentioned above, and of the methods described herein may also be adapted to integrate ECG and location data which may allow the methods and systems to customize feedback to the user based on local medical providers (e.g., physicians). For example, any of the methods or systems may include or be adapted to perform any of the steps including: receiving, from a user, cardiac data and location data of the user; and generating a list of medical specialists and medical specialist locations from a database of medical specialists and medical specialist locations, wherein the list is generated in response to the received user cardiac and location data. The method or system may also include sorting the generated list in response to one or more of the received user cardiac data or received user location data. The sorted list may be sorted, for example, by one or more of: proximity to the user, availability, experience, patient rating score, insurance accepted, affiliation with a medical provider network, or price of service.

As mentioned above, the apparatuses and methods described herein can facilitate such remote professional or specialist interpretation by sorting medical data into groups (or bundles) and determining which medical data bundles are appropriate for interpretation for sub-groups of professionals or specialists. For example, a winning "bid" based on professional or specialist location, specialty, expertise, experience, and/or price information can be determined, and the medical professional or specialist sub-group supplying the winning bid may be allowed to interpret a selected medical data bundle. While many current outsourcing professionals or specialists belong to individual outsourcing centers located at a central location, the sub-groups of medical professionals or specialists using the systems herein need not belong to an individual outsourcing center and individual medical professionals or specialists can be located in a variety of locations so long as a winning bid is placed and he or she has access to the medical data bundle. Bids can be placed through the Internet, a cellular data network, or other wide area network. In at least some cases, only medical professionals or specialists who have gone through a certification or membership process, by paying membership fees and going through a background check, for example, are allowed to place bids. This location and/or outsourcing center independence can allow the remote interpretation and diagnosis of medical information to be scaled to support a large patient population (e.g., millions to billions) more easily than traditional, more centralized medical data outsourcing centers.

The apparatuses and method described herein are generally helpful for interpretation of cardiac data of a user, such as an electrocardiogram (ECG). A remote server, for example, may receive cardiac data of a plurality of users and a plurality of bids from a plurality of medical specialists. The cardiac data and/or the plurality of bids may be received from a plurality of mobile computing devices of the plurality of users. These mobile computing devices may comprise smartphones, tablet computers, wearable computing devices, or the like. The remote server may select a medical specialist subgroup of the plurality of medical specialists. A plurality of bids may be received from the plurality of computing devices of the plurality of medical specialists. To select the medical specialist subgroup, a winning bid associated with an individual medical professional (or subgroup) may be determined from the received plurality of bids. A cardiac data interpretation can comprise a diagnosis of the cardiac data.

The apparatuses and methods described may provide an interpreted cardiac parameter to a subject. In particular, a cardiac parameter may be interpreted by a human (e.g., by a technician, a specialist, a physician, or the like). This interpretation may be in addition to (e.g., following triage by)

interpretation or modification of the cardiac parameter (e.g., ECG) by a machine (e.g., using an appropriate algorithm.) The cardiac parameter of a subject may be received, by a remote server for example, from a cardiac parameter sensing system prescribed to the subject by a prescribing physician. A plurality of medical professionals may be provided access to the cardiac parameter received by the remote server. An interpretation of the sensed cardiac parameter may be sent to the subject, for example, back to the local computing device of the subject. The interpretation may be generated by one or more medical professionals of the plurality of medical professionals other than the prescribing physician. These medical professionals may provide the interpretations from a variety of locations remote from one another.

A cardiac parameter sensing system may comprise a local computing device, such as a personal computer, a laptop computer, a palm top computer, a smartphone (e.g., an Apple iPhone, a Samsung Galaxy S phone, a Google Nexus phone, or the like), tablet computer (e.g., an Apple iPad, a Samsung Galaxy Tab tablet, a Google Nexus tablet, or the like), or wearable computer (e.g., a Google Glass), and a sensor in communication with the local computing device such as those described in commonly owned U.S. patent application Ser. No. 12/796,188 (now U.S. Pat. No. 8,509,882), Ser. Nos. 13/108,738, 13/420,520 (now U.S. Pat. No. 8,301,232), Ser. Nos. 13/752,048, 13/964,490, 13/969,446, and 14/015,303 and U.S. Provisional Applications Nos. 61/812,655, 61/845,254, 61/872,555, 61/874,806, and 61/898,330, the full disclosures of which are incorporated herein by reference. Alternatively or in combination, the sensor may be a built-in component of the local computing device. The cardiac parameter may be received from the local computing device which may later receive the interpretation sent by the remote server.

A prescribed cardiac parameter sensing system may be configured to perform the function of one or more cardiovascular diagnostic and/or monitoring devices such as an arrhythmia detector and alarm (including ST-segment measurement and alarm), an arrhythmia detector and alarm, a patient monitor physiological (with arrhythmia detection or alarms), an ST segment monitor with alarm, an implantable cardiac event recorder (with arrhythmia detection), an extravascular blood flow probe, a laser blood flow kit, a cardiac monitor (including cardiotachometer and rate alarm), a low patient acuity monitoring system, a patient monitor physiological (without arrhythmia detection or alarms), an apex cardiograph (vibrocardiograph), a ballistocardiograph, an echocardiograph, an electrocardiograph, an ST segment monitor, a single lead over-the-counter electrocardiograph, an electrocardiograph electrode, a multi-function electrocardiograph electrode, a phonocardiograph, a vectorcardiograph, a medical magnetic tape recorder, an ambulatory electrocardiograph with analysis algorithm, an ambulatory (without analysis) electrocardiograph, an apex cardiographic transducer, or heart sound transducer. The prescribed cardiac parameter sensing system may be configured with downloaded software (e.g., an "app" downloaded to the local computing device to be executed by the processor of the local computing device), removably attached physiological parameter sensor(s), and/or built-in physiological parameter sensor(s) to configure the local computing device to perform the function of one or more of the aforementioned cardiovascular diagnostic and/or monitoring devices.

A cardiac parameter may be at least partially interpreted automatically (e.g., by using the software application provided on, or the "app" downloaded to, the local computing device and executed using a processor of the local computing device). For example, a first portion of the interpretation can be performed automatically and a second portion of the interpretation can be performed by a human. Alternatively or in combination, the interpretation can be substantially (e.g., fully) automated.

The cardiac parameter sensing system may perform a plurality of the above-mentioned cardiovascular diagnostic and/or monitoring functions. In many embodiments, the cardiac parameter sensing system may restrict a subset of such functions if those functions have not been prescribed for. Other functions may not require a prescription. For example, the cardiac parameter sensing system may not need a prescription to generate a single-lead electrocardiograph but may require a prescription to measure an ST-segment of an electrocardiograph or detect arrhythmia and generate an alarm. The prescribing physician may prescribe the cardiac parameter sensing system to the user for the restricted function(s) and the prescription may be entered (e.g., into the downloaded "app" of the local computing device) into the cardiac parameter sensing system to unlock one or more of the restricted cardiovascular diagnostic and/or monitoring functions. The unrestricted and restricted set of cardiovascular diagnostic and/or monitoring functions may or may not overlap (e.g., one or more features of the sets of features can be the same, or the sets of features can be different). The unrestricted and restricted sets may or may not comprise the same cardiac parameter(s).

A local computing device may be configured to receive the sent interpretation and display the interpretation, for example on a display of the local computing device through a user interface which may be downloaded from the Internet (e.g., provided on the software application or "app") or other wide area network such as a cellular data network. The user interface may be downloaded from an application distribution service or platform. The user interface may comprise a component of a mobile application or mobile app and the application distribution service may be an Internet-accessible service such as Apple iTunes, Google Play, Amazon Appstore, or the like. Generally, the cardiac parameter comprises an electrocardiogram (ECG) and the interpretation comprises a diagnosis.

The apparatuses (e.g., systems) and methods described herein may also include apparatuses and methods for analyzing cardiac data of a user. A remote server, for example, receives cardiac data of a user transmitted from a local computing device removably coupled to a protective case. The protective case may comprise a sensor configured for sensing the cardiac data and transmitting the sensed cardiac data to the local computing device. The local computing device may comprise any of the local computing devices described herein. A medical specialist may be provided access to the received cardiac data at the remote server. The remote server may then receive a medical specialist interpretation of the accessed cardiac data. The remote server may then send the received cardiac data interpretation from the remote server to the local computing device for display on a display of the local computing device. The display may show a user interface of an application downloaded from an application distribution service or platform as described herein. The remote server may store one or more of the received cardiac data from the local computing device or the received medical specialist interpretation of the accessed cardiac data. Access may be provided, from the local computing device, to the stored medical specialist interpretation of the accessed cardiac data. Through the local computing device, the user may be notified that the server has received the medical specialist interpretation.

As mentioned above, cardiac data may include an electrocardiogram (ECG) measured by the sensor of the protective case and may further comprise user location data provided by the local computing device such as with a GPS transceiver. The remote server may compile a list of local medical specialists in response to the location information from the local computing device, and further comprising providing the user with the list. This list may be sent to the local computing device for display, and the local computing device may facilitate the scheduling of an appointment with one of the local medical specialists provided to the user. The cardiac data sent by the local computing device may also include notes input by the user, data regarding user symptoms, data regarding an activity level or the user, and the like.

The apparatuses (e.g., systems) and a methods described herein may also include apparatuses and methods for managing cardiac data, electrocardiogram (ECG) data, for example, of a user. A remote server, for example, may receive from the user cardiac data and location data of the user. In response to the received user cardiac and location data, the remote server may generate a list of medical specialists and medical specialist locations from a database of medical specialists and medical specialist locations. The list of medical specialists may comprise one or more of a list of cardiac technicians or specialists. The generated list may be transmitted by the remote server to the user, for example, through the Internet, a cellular data network, a wide-area-network, or the like. The user may receive the list through his or her smartphone, tablet computer, wearable computer, or the like. This device may be instructed to display the generated list on a display of the smartphone. The transmitted location data may comprise GPS data and may include the latitude and longitude of the user. The generated list may be sorted in response to one or more of the received user cardiac data or received user location data. The list may be sorted by one or more of proximity to the user, availability, experience, patient rating score, insurance accepted, affiliation with a medical provider network, or price of service.

DETAILED DESCRIPTION

Embodiments of the invention include systems, devices and methods for processing, distributing, and analyzing data. Embodiments of the invention also include systems, devices and methods for processing and distributing tasks or jobs for completion by a qualified worker or specialist. In one embodiment, crowdsourcing data to specialists for interpretation can be accomplished using an auction system to match the specialists with discrete portions of the data. The data can be bundled based on one or more categories or characteristics, and then placed on an auction where the specialists can bid for each bundle by submitting a payment price. In some embodiments, the data can be medical data, such as ECG data, imaging data and test data, for example.

In some embodiments, such systems, devices and methods can be used to process, distribute and analyze ECG data. The ECG data can be generated by a traditional ECG recording device, or an ambulatory ECG recording device such as a Holter monitor or an event recorder. Event recorders include traditional event recorders as well as mobile, i.e. smartphone, based event recorders. The ECG data can be transmitted over phone lines, the cellular network, the mobile data network, or through a Wi-Fi network, for example, to a central processing center and/or directed to a medical professional, such as a physician. As more and more users adopt traditional and mobile event recorders, more and more ECG data will be generated. In some embodiments, the user can elect to have their ECG data interpreted by a specialist. In some embodiments, the user can be prompted by the event recorder whether the user would like his or her ECG data interpreted by a specialist. In some embodiments, the user can elect to send the ECG data to be interpreted by a specialist. In some embodiments, before sending out the ECG data to the server or cloud, the user or patient must confirm his or her consent to send out the ECG data. In some embodiments, the user can input data regarding their condition or status at the time the ECG is taken that is associated to and sent with the ECG data. For example, the user can input symptoms felt before and/or during the ECG recording, and can input the activities the user was engaged in preceding and/or during the ECG recording. In some embodiments, if the user can be charged a predetermined amount for an interpretation of his or her ECG data. In some embodiments, the user can pay a monthly fee for the ability to have a predetermined number of ECGs interpreted by a specialist.

A physician with many patients may not have the ability, bandwidth or desire to analyze all of their patients' ECG data. Accordingly, in some embodiments, it may be desirable to process and distribute the ECG data to a group of qualified specialists. For example, the ECG data can be distributed to cardiac technicians and/or physicians such as cardiologists and electrophysiologists for interpretation. In some embodiments, the cardiac technicians can be assigned to sort and triage individual ECGs into a plurality of groups, such as normal ECGs and abnormal ECGs. In some embodiments, the cardiac technicians or other specialists bid upon uncategorized ECG bundles as described below, and winning bidder are assigned to triage the ECGs in the uncategorized bundle. In some embodiments, the abnormal ECGs can be further subdivided into critical ECGs and non-critical ECGs. The ECG groups can be ranked or prioritized such that abnormal ECGs and critical ECGs are given a higher priority for quicker processing than normal ECGs.

In some embodiments, a computer system and method can be used to triage and categorize the ECGs. In some embodiments, the algorithm can identify typical ECG abnormalities using a pattern recognition algorithm. For example, the pattern recognition algorithm can identify abnormal P waves, T waves or QRS complexes. In some embodiments, the algorithm can be a beat classification algorithm. The computer system can include a server and a database, for example. The server can have one or more processors for executing instructions and memory for storing the instructions. The instructions can be encoded in software and/or hardware such as ASICs. The instructions can encompass any of the methods and steps described herein.

In some embodiments, the specialists are certified. Appropriate certification for interpretation of ECGs include, for example, medical board certification for physicians in cardiology and/or electrophysiology and certification for cardiovascular technology for cardiac technicians. In some embodiments, the physicians can be board certified and the cardiac technicians do not have to be certified. Requiring only the physicians to be certified can make sense in embodiments where the cardiac technicians are sorting and triaging the ECGs for review by a physician.

In some embodiments, each group of ECG data can be bundled into a predetermined number of ECGs. For example, a bundle of ECG data can have between 5 to 100 ECGs in increments of five. In some embodiments, a bundle of ECG data can have at least 5 to 100 ECGs in increments of five. In some embodiment, a bundle of ECG data can have no more than 5 to 100 ECGs in increments of five. For example, normal ECGs can be bundled into sets of 25 normal ECGs, and abnormal ECGs can be bundled into sets of 25 abnormal ECGs. In some embodiments, the number of abnormal ECGs bundled together is less than the number of normal ECGs bundled together. This may allow the abnormal ECGs to be distributed among a larger number of specialists and enable a quicker turnaround time for interpretation of the abnormal ECGs.

In some embodiments, the bundled ECGs can be listed on an online auction house. Registered specialists can bid on the bundled ECGs by specifying an amount the specialist is willing to be paid in exchange for interpreting the ECGs. In some embodiments, the online auction house can retain the difference between the amount charged to the users and the amount bid by the specialist that wins the auction. In some embodiments, the ECG bundles can have a maximum bid amount, which is a maximum amount that can be paid to a specialist for interpreting the bundle. In some embodiments, an abnormal ECG bundle can have a higher maximum bid amount than a normal ECG bundle to provide additional incentives for specialists to bid on the abnormal ECG bundles.

In some embodiments, the online auction house determines the winning bid by selecting the lowest bid amount as the winning bid. In other words, the specialist that is willing to be paid the lowest amount for interpreting the ECG bundle wins the auction. In some embodiments, the bids can also be sealed or concealed such that each bidder is unaware of the amounts bid by other bidders, such as in a first-price sealed-bid auction. In some embodiments, the auction can be conducted according to a second-price sealed-bid auction, i.e. a Vickrey auction, when the bids are sealed and the bidder submitting to lowest bid wins but is paid the amount bid by the second lowest bidder. In some embodiments, the auction is conducted according to an open descending bid auction, i.e. an English auction, where the bidders are aware of the lowest bid, and the bidding continues until only one bidder remains, or the period for bidding expires. The lowest bidder that remains or the bidder with the lowest bid when the period for bidding expires wins the auction. In some embodiments, the auction is conducted according to an open ascending bid auction, i.e. a Dutch auction, where the price starts at a predetermined floor level that can be based on the category of the ECG bundle and the size of the bundle, among other factors. The price is progressively raised until a bidder accepts the price and submits a bid, thereby winning the auction and getting paid at the bid price for interpreting the ECG bundle. In some embodiments, the online auction house can run one or more different types of auctions. In some embodiments, the auction can include a buyout price which is a price that wins the auction if bid by a specialist. In some embodiments, the buyout price can be lower for normal ECG bundles and higher for abnormal ECG bundles.

In some embodiments, the bidding is open for a relatively short period of time in order to keep turnaround time low. For example, the bidding period can be set at less than 15, 30, 45 or 60 minutes, or less than 1, 2, 3, 4, 5, 6, 12, or 24 hours. In some embodiments, the user or patient can elect for a quicker turnaround time for interpreting his or her ECG, such as having the ECG interpreted within 1, 2, 3, 4, 5, 6, 12, 24, 48, or 72 hours for example, which provides some bounds for the bidding period and the time given to the specialists for interpretation. In the event that no bids are placed on an ECG bundle, the ECG bundle can be sent to a contracted group of cardiac technicians and/or physicians, i.e. specialists, for interpretation as a predetermined rate.

In some embodiments, the ECGs can be additionally sorted by location of the user or patient, such that an ECG bundle comprises ECGs from users or patients located in the same geographic location or area. In some embodiments, the ECG data can be geotagged to include location data, such as GPS data which can include latitude and longitude information, which can be converted to a geographical location or area. For example, smartphones and other devices with a GPS receiver can provide the GPS data and can be integrated or associated with the ECG recorder. In some embodiments, the ECG data can be geotagged to include location data specified by the user. For example, the user can set up a user profile that includes location data, such as street, city, state, zip code and the like, which can be retrieved and associated with the ECG data before it is sent for bundling.

In some embodiments, the online auction house can allow the specialists to sort the ECG bundles according one or more categories. These categories can include the type of ECGS included in the bundles, i.e. normal or abnormal ECGs, and the geographical location or area associated with the ECG bundle. In some embodiments, the auction house by default lists and displays to the specialist ECG bundles that were acquired from users and patients in the same geographic location or area. Additionally, the ECGs can be bundled and sorted in the auction house by the date and time the ECG data was acquired. In some embodiments, to promote bidding on older ECG bundles, incentives based on the acquisition date of the ECG data or the time the ECG bundles was posted on the auction house can be provided. For example, a time based premium can be paid on top of the winning bid price to the specialist that wins the auction. In some embodiments, the premium can be between 0 to 100%, 0 to 75%, 0 to 50%, or 0 to 25% of the bid price. The premium can increase according to a predetermined schedule based on the time that the ECG bundle has been listed on the auction house, or the length of time since the ECG data was acquired, or a combination of the two, for example.

The specialist that wins the auction for a particular ECG bundle can be sent or provided access to the ECG bundle. For example, the specialist can be provided instructions for remotely logging into a secure and HIPAA compliant computer system or database for access and retrieval of the ECG bundle. In some embodiments, the specialist is contracted to interpret the ECGs in the bundle within a predetermined amount of time. For example, the specialist can be contracted to interpret the ECGs within 48, 36, 24, 12, 8, 4, 2 or 1 hours. As mentioned above, ECG bundles containing ECGs categorized as abnormal or critical can be contracted to be interpreted within a relatively short period of time, such as within 1, 2, 4, 8, 12 or 24 hours.

In some embodiments, the specialists can provide an analysis of the ECGs as part of the interpretation. The ECG can be confirmed or determined to be normal or abnormal. If abnormal, the portions of the ECG that appear to be abnormal can be indicated and/or notated with an explanation of the abnormality. In some embodiments, the specialist can provide a preliminary diagnosis regarding the potential cause of the abnormality. In some embodiments, all the analysis, notations and comments can be entered directly into the HIPAA compliant computer system or database by the specialist. In some embodiments, after the specialist has finished interpreting the ECG, the specialist can indicate to the computer system that the interpretation is complete by closing out the ECG and confirming completion. In some embodiments, the patient can be immediately sent a notification that the interpretation is complete. In some embodiments, the patient is not sent back the complete analysis or the annotated ECG, but instead is sent a summary of the analysis. For example, the summary can inform the patient whether the ECG is normal or abnormal, and can provide the patient with a recommendation to seek further medical attention if the interpretation of the specialist indicates an abnormal or critical ECG. In some embodiments, the patient can also be provided with the specialists' analysis and/or the annotated ECG. In some embodiments, the patient can be prompted or have the option to forward the interpretation of the ECG, including the complete analysis and annotated ECG, to the patient's physician or to a physician recommended by the computer system, as set forth above. In some embodiments, the physician that is forwarded the patient's ECG is provided access the secure HIPAA compliant computer system where the physician can also access the interpreted ECG.

In some embodiments, the patient's ECG data can be stored in a database or on the cloud. As the patient acquires more and more ECG data, the patient's ECG data history can be compiled. In some embodiments, the ECG data can be integrated or incorporated into the patient's electronic health or medical records. In some embodiments, the interpreted ECG data in the database or cloud can be used to refine the triage algorithms. In particular, ECGs that were assigned the wrong category by the triage algorithm can be analyzed to refine the triage algorithm. In some embodiments, the interpreted ECG data can be compared with other ECG data in the database or cloud, taking into account data input by the user regarding the condition and status of the user during and/or before the ECG recording.

In some embodiments, a quality control system and method can be implemented to monitor the performance of the specialists in ECG interpretation. In some embodiments, one or more reference quality control (QC) ECGs can be included in each ECG bundle. The QC ECGs can include either normal ECGs or abnormal ECGs or both types. In some embodiments, the system scores the interpretation of the QC ECGs by the specialists. In some embodiments, each specialist can have a QC score that can be based on all the QC ECGs interpreted by the specialist, or can be a score based on the last predetermined number of QC ECG interpretations, such as the last 5, 10, 15, 20, 25, 50, 75, or 100 QC ECG interpretations. In some embodiments, specialists must maintain a QC score above a minimum threshold, such as above 75-95% for example, in order to be allowed to participate in the auction house system. In some embodiments the QC system can send the same patient ECG to a plurality of specialists, and the system can determine whether the interpretation of the different specialists is consistent. For example, the QC system can send a patient ECG to 3 or more specialists, and if one specialist or a minority of specialists disagrees with the majority, those minority specialists can be identified. If a specialist is in the minority above a predetermined threshold frequency, i.e. the specialist can be excluded from participating in the online auction house.

In some embodiments, the patient can be referred to the local specialist that interpreted the patient's ECG data if the patient asks for a referral or if the patient's ECG is abnormal and requires medical attention or further evaluation. In some embodiments, the patient can be prompted to see a health care professional for further evaluation or treatment depending on interpretation of the patient's ECG. In some embodiments, the patient can be referred to any local specialist, and not just the specialist that interpreted the patient's ECG, from the pool of specialists that participates or is registered with the auction house system. In some embodiments, the patient can be provided with a list of specialists that are local. The list can include the specialist that interpreted the patient's ECG and can further include other local specialists. The list of specialists can be sorted by the patient using a variety of criteria, including proximity to the patient, availability, experience, patient rating score, insurance accepted, affiliation with HMO, hospital or other medical provider network, price of services and the like. In some embodiments, the patient can be referred to local hospitals, emergency rooms, or health clinics. In some embodiments, the patient can be provided with contact information and location information of the health service provider and can be given the option and ability to schedule an appointment.

Figure 1:
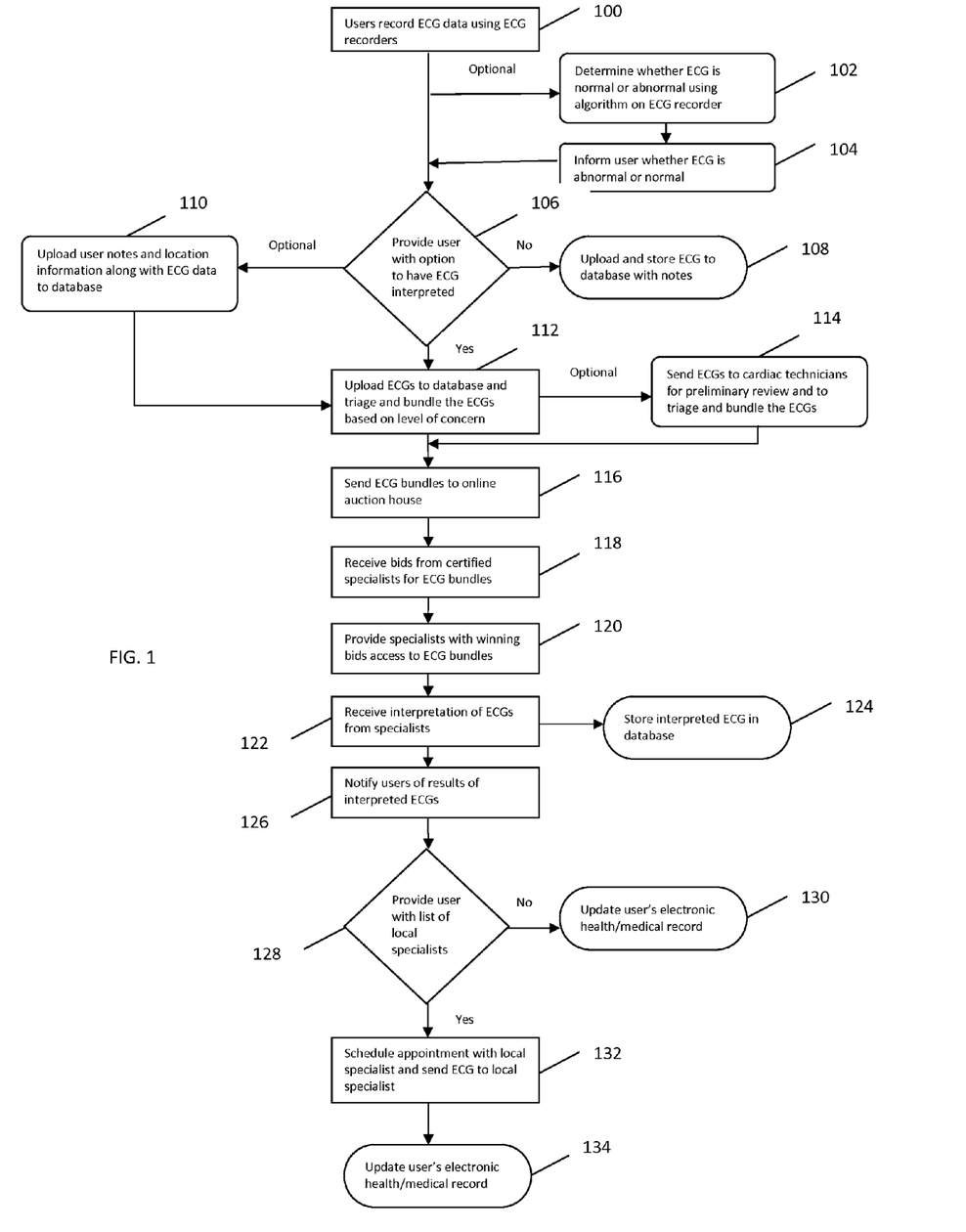
FIG. 1 is a flow chart that illustrates an embodiment of the overall systems and methods of triaging, bundling, and auctioning ECG data to specialists for interpretation.

FIG. 1 is a flow chart that illustrates an embodiment of the overall systems and methods described herein. For example, at block 100 the users record ECG data using ECG recorders. In some embodiments, the ECG recorder optionally triages and categorizes the ECG as normal or abnormal using an algorithm, as illustrated in block 102, and then can optionally inform the user whether the ECG has been preliminarily categorized as abnormal or normal by the algorithm, as shown in block 104. Next, in block 106 the system and method provides users with the option to have their ECG interpreted by a specialist. If the user declines the option to have the ECG interpreted, the system and method can send or upload the ECG to a database, as shown in block 108. The user can also enter in notes to provide context to the ECG, describing symptoms and/or circumstances surrounding the ECG, for example.

If the user accepts the option to have the ECG interpreted and provides consent to release the ECG to specialists, the ECG can be sent to a server and database, where the ECG can be triaged, categorized and bundled according to predetermined criteria, such as level of concern, as illustrated in block 112. Levels of concern can include any combination of normal, abnormal, and critical, for example. The ECGs can be categorized and triaged by an algorithm on the server or can alternatively be triaged and categorized by cardiac technicians in a preliminary review, as shown in block 114. The user can also optionally enter notes to provide context to the ECG, including symptoms, circumstances and location information, which can also be provided automatically through, for example, a GPS device in the ECG recorder, as shown in block 110.

After the ECGS are bundled based according to the predetermined criteria, the ECG bundles can be sent to an online auction house, as shown in block 116. The auction can be conducted according to any number of auction types as described above. Bids for the bundles can be received from registered and certified specialists, as shown in block 118. The server determines the winner of the auction for each bundle according the rules of the auction and can provide access to the bundle to the winning bidder, as shown in block 120.

Specialists with winning bids can be given access to the bundles through a variety of ways, such as being provided secured online access to the bundle. For example, the specialist can log into his or her registered account using a secure username and password and access bundles in which the specialist was the winning bidder. The specialist can then interpret the ECGs and provide the interpreted ECGs back to the server with their notes and comments, as shown in block 122. For example, in one embodiment, the specialist can review the ECGs in the bundle through an online interface, which allows the server to receive real-time interpretations from the specialist as each ECG is interpreted rather than only receiving the results after the entire bundle has been interpreted. In the event the specialist will not have continuous internet access or will only have intermittent internet access, the specialist can be provided the option of downloading the ECG bundle to be reviewed offline. When the specialist logs back online, the interpreted ECGs can be automatically uploaded to the server or manually uploaded to the server. After receiving the interpreted ECGs, the server can then store the interpreted ECGs in a database, as shown in block 124.

As the server receives interpreted ECGs, the server can notify users of the results of their interpreted ECGs, as shown in block 126. In some embodiments, users may be provided with just a summary of the interpretation, such as whether the ECG was normal, abnormal or critical, for example, and provide the user with a recommendation base on the interpretation. In some embodiments, the users may be additionally provided access to the complete interpretation provided by the specialist. The user can also be provided with a list of local specialists that can provide additional medical services, if desired, as shown in block 128. The server can determine the user's location based on one or more factors, including a location specified in the user's registration profile or location data attached to the ECG by either the user or automatically through a GPS based device, for example, and then provide a list of local specialists based on the determined location or locations. The user can decline contacting a specialist from the list, in which the server can optionally update the user's electronic health or medical record as shown in block 130. Alternatively, the user can elect to schedule an appointment with one or more of the local specialists provided on the list, as indicated in block 132. The server can automatically send the user's ECG to the selected local specialist, or the selected local specialist can be provided online access to the user's ECG via, for example, the user's updated electronic health or medical record, as shown in block 134.

Figure 2:
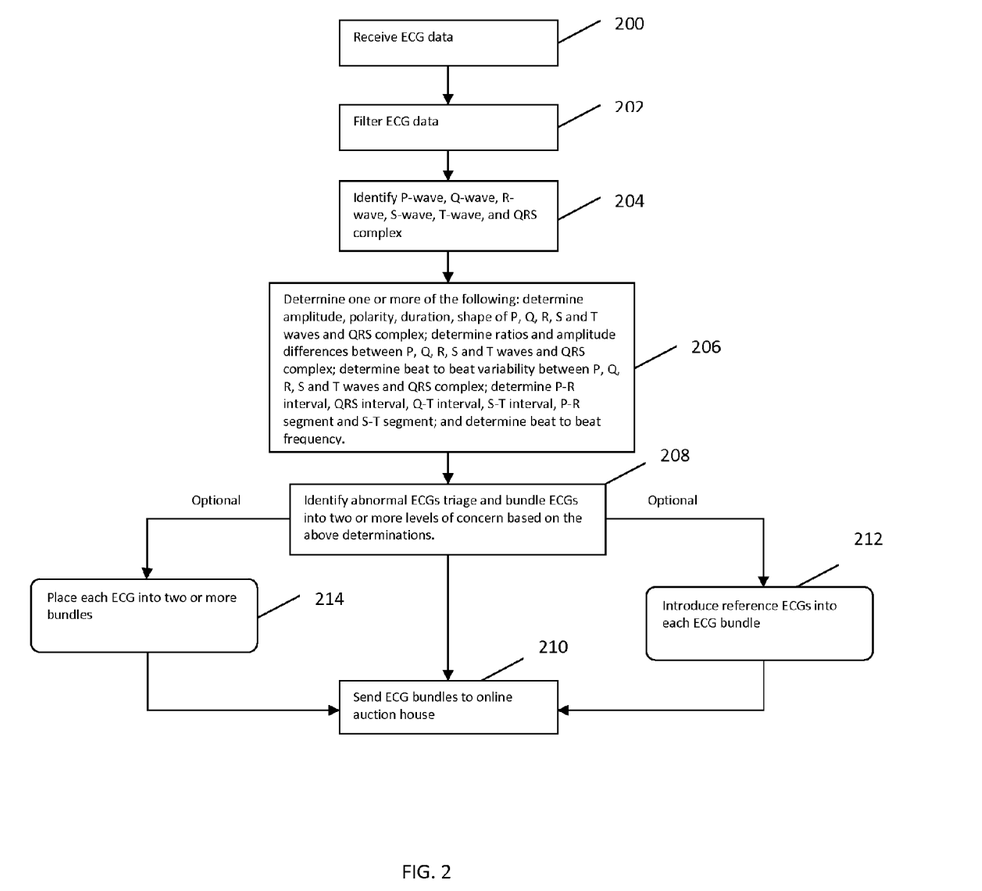
FIG. 2 is a flow chart that illustrates an embodiment of a system and method of triaging ECGs.

FIG. 2 is a flow chart that illustrates an embodiment of a system and method for triaging, categorizing and bundling ECGs using an algorithm and can be integrated into the flow chart illustrated by FIG. 1. The system and method can be implemented on the ECG recorder in part, and/or can be implemented on a server and database that receives all the ECGs, as shown in block 200. The ECG data can be filtered to remove signal noise, as shown in block 202. Next, the P-wave, Q-wave, R-wave, S-wave, T-wave, and/or QRS complex can be identified, as shown in block 204. Once the various components of the ECG have been identified, one or more of the following ECG features can be determined and extracted as shown in block 206: amplitude, polarity, duration, shape of the P, Q, R, S and T waves and QRS complex; ratios and amplitude differences between P, Q, R, S and T waves and QRS complex; beat to beat variability between P, Q, R, S and T waves and QRS complex; P-R interval, QRS interval, Q-T interval, S-T interval, P-R segment and S-T segment; and beat to beat frequency. Based on these determined features, the algorithm can triage, categorize and bundle the ECGs into different levels of concern as shown in block 208. The ECG bundles can then be sent to the online auction house as shown in block 210. Optionally, before the ECG bundles are sent to the online auction house, reference ECGs can be introduced into each ECG bundle as shown in block 212 and/or each ECG can be placed into two or more bundles as shown in block 214.

Figure 3:
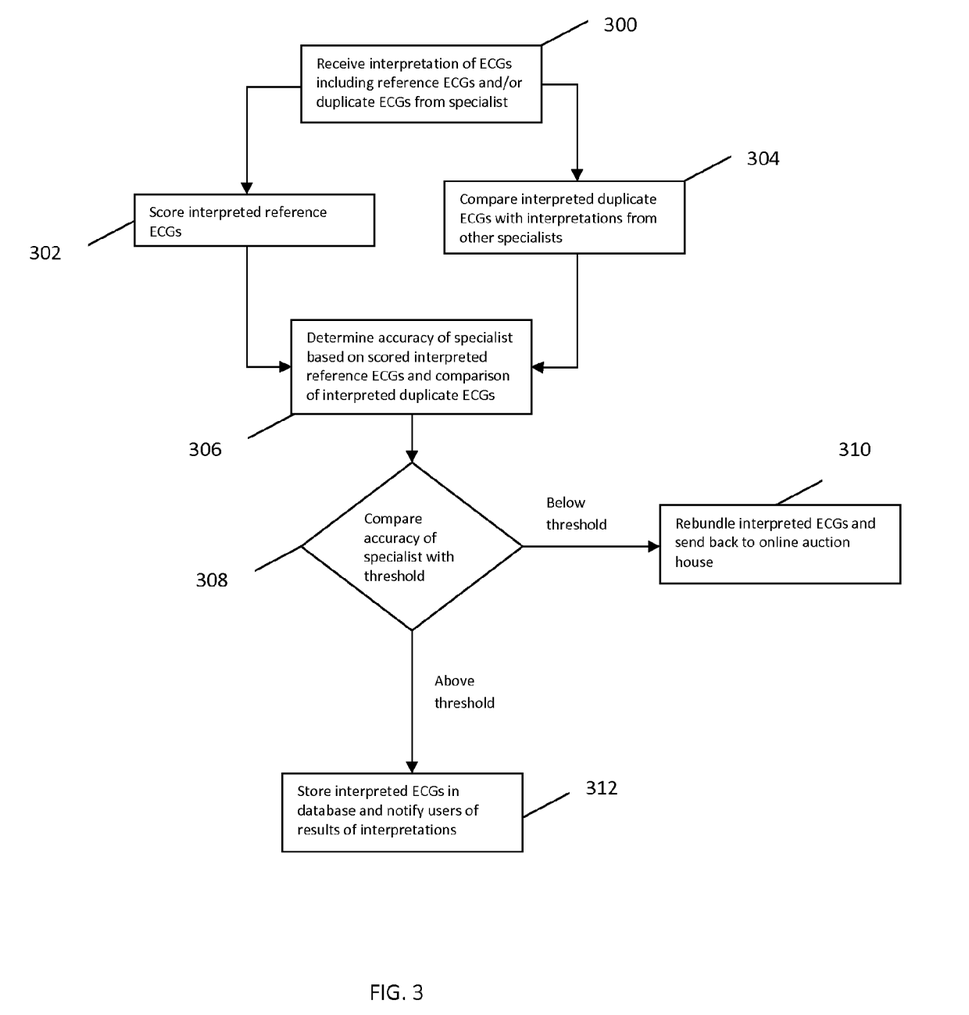
FIG. 3 is a flow chart that illustrates an embodiment of a system and method for determining the accuracy of a specialist's interpretation of ECG data.

FIG. 3 is a flow chart that illustrates an embodiment of a system and method for assessing the quality and accuracy of a specialist's ECG interpretations when the ECG bundles include reference ECGs and/or duplicate ECGs as described in FIG. 2. As the specialist interprets the reference and duplicate ECGs, and if needed uploads the interpreted ECGs to the server, the server can score the interpreted reference ECGs by, for example, comparing the specialist's interpretation to the correct interpretation as shown in block 302. In addition or alternatively, the server can compare the specialist's interpretations of duplicate ECGs with interpretations from other specialists to determine whether the interpretation of the specialist is consistent with the interpretations of other specialists or is an outlier, as shown in block 304. The accuracy of the specialist can be determined based on the scored interpreted reference ECGs and the comparison of the interpreted duplicate ECGs with the interpretations of other specialists as shown in block 306. The accuracy of the specialist can then be compared with a predetermined threshold at regular intervals or each time the specialist interprets an ECG as shown in block 308. If the specialist's accuracy is below the threshold, a predetermined number of ECGs and/or ECGs that are subsequently interpreted by the specialist can be rebundled and sent back to the online auction house for reinterpretation as shown in block 310. If the specialist's accuracy is above the predetermined threshold, as shown in block 312, the server can store the interpreted ECGs in the database, update the users' electronic heath or medical records, and notify users of the interpretations as indicated in FIG. 1.

Although the above steps show methods for managing ECG and other cardiac data from a plurality of users or patients in accordance with many embodiments, variations of these methods and systems may be based on the teaching described herein. The steps described herein may be completed in a different order. Steps may be added or deleted. Steps and sub-steps of the various methods described herein may be substituted for each other or otherwise added into the various methods, for example. Many of the steps may be repeated as often as beneficial.

In general, as mentioned above, any of the methods described herein may be implemented as an apparatus, including in particular an apparatus including a processor having non-transitory computer-readable storage medium storing a set of instructions capable of being executed by a processor, that when executed by the processor causes the processor to perform any of these steps. For example, one or more of the steps of the methods described herein for managing ECG and other cardiac data from a plurality of users or patients may be performed with circuitry or a processor of a computing device, for example, of one or more remote servers or one or more computing devices local to a user or patient. The circuitry or processor may be programmed to provide one or more of the steps of the methods described herein, and the program may comprise program instructions stored on a computer readable memory or programmed steps of the circuitry or processor.

Although the many embodiments described herein are directed to the management of ECG and other cardiac data from a plurality of users, a person of ordinary skill in the art will recognize that the methods and systems described herein may be applicable for a variety of other medical data as well. Such medical data may include medical imaging data, such as visual images, x-rays, MRIs, ultrasound scans, CT scans, PET scans, and the like. Alternatively or in combination, such medical data may include medical data which may be conveniently taken using a local computing device of the user such as fitness data, activity data, sleep data, blood oxygenation data, glucose level data, and the like. The methods and systems described herein may be applied to sort the multitude of data and facilitate a large group of medical specialists interpreting or diagnose the sorted data by determining which medical specialist subgroup(s) are allowed to provide such interpretation or diagnosis.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. For example, features described in one embodiment can be used in another embodiment. The embodiments were chosen and described in order to best explain the principles of the invention and its practical application, to thereby enable others skilled in the art to best utilize the invention and various embodiments with various modifications as are suited to the particular use contemplated.

What is claimed is:

1. A method for analyzing ECG data, the method comprising:
    receiving ECG data from a plurality of users in a server having a processor and memory;
    categorizing, using the processor, the ECG data into groups based on extracted ECG features;
    listing the categorized ECG groups by category on an online auction house;
    receiving bids for the listed ECG groups from registered specialists;
    determining, using the processor, which specialist won a bid for a group from the listed ECG groups;
    providing the specialist that won the bid for the group with access to the ECGs within the group; and
    inserting at least one reference ECG in each ECG group; determining an accuracy of the received interpreted ECG data based on the specialists' interpretation of the reference ECG; and re-listing the group of ECGs on the online auction house when the accuracy is below a predetermined threshold.

2. The method of claim 1, further comprising receiving interpreted ECG data from the specialist for the ECGs within the group.

3. The method of claim 1, further comprising extracting, using the processor, a plurality of ECG features from the ECG data.

4. The method of claim 1, wherein receiving comprises receiving ECG data including extracted ECG features from the plurality of users.

5. The method of claim 1, wherein categorizing comprises categorizing the ECG data into groups based on extracted ECG features including location information.

6. The method of claim 1, wherein categorizing comprises categorizing the ECG data into groups based on extracted ECG features including user annotations.

7. The method of claim 1, wherein categorizing comprises categorizing the ECG data into groups based on extracted ECG features including one or more of: amplitude, polarity, duration, or shape of the P, Q, R, S and T waves and QRS complex; ratios and amplitude differences between P, Q, R, S and T waves, or QRS complex; beat to beat variability between P, Q, R, S and T waves, or QRS complex; P-R interval; QRS interval; Q-T interval; S-T interval; P-R segment; S-T segment; and beat to beat frequency.

8. The method of claim 1, further comprising inserting at least one reference ECG in each ECG group.

9. The method of claim 1, further comprising inserting at least one reference ECG in each ECG group; and determining an accuracy of the received interpreted ECG data based on the specialists' interpretation of the reference ECG.

10. The method of claim 1, further comprising notifying a user that the user's ECG data has been interpreted.

11. The method of claim 1, further comprising providing a user with a list of local specialists based on location information provided with ECG data from the user.

12. The method of claim 1, further comprising storing the ECG data and the interpreted ECG data in a database.

13. A method for analyzing ECG data, the method comprising:
    receiving ECG data from a plurality of users in a server having a processor and memory;
    categorizing, using the processor, the ECG data into groups based on extracted ECG features;
    listing the categorized ECG groups by category on an online auction house;
    receiving bids for the listed ECG groups from registered specialists;
    determining, using the processor, which specialist won a bid for a group from the listed ECG groups;
    providing the specialist that won the bid for the group with access to the ECGs within the group; and
    duplicating a user's ECG data between two or more groups; and re-listing the two or more groups of ECGs on the online auction house when the agreement between the interpreted ECG data for the duplicated ECG data is below a predetermined threshold.

14. A method for analyzing ECG data, the method comprising:
    receiving ECG data from a plurality of users in a server having a processor and memory;
    categorizing, using the processor, the ECG data into groups based on extracted ECG features;
    listing the categorized ECG groups by category on an online auction house;
    receiving bids for the listed ECG groups from registered specialists;
    determining, using the processor, which specialist won a bid for a group from the listed ECG groups;
    providing the specialist that won the bid for the group with access to the ECGs within the group; and
    scheduling an appointment for a user, using the processor, with a local specialist.

15. A non-transitory computer-readable storage medium storing a set of instructions capable of being executed by a processor, that when executed by the processor causes the processor to:
    receive ECG data from a plurality of ECG recording devices;
    categorize the ECG data into a plurality of groups based on extracted ECG features;
    list the ECG groups by category on an online auction house;
    receive bids for the listed ECG groups from registered specialists;
    determine which specialist won a bid for a group from the listed ECG groups;
    provide the specialist that won the bid for the group with access to the ECGs within the group; and
    wherein the set of instructions, when executed by the processor, further causes the processor to determine an accuracy for the specialist and re-list the ECG group on the online auction house if the accuracy is below a threshold.

16. The non-transitory computer-readable storage medium of claim 15, wherein the set of instructions, when executed by the processor, further causes the processor to receive interpreted ECG data from the specialists.

17. The non-transitory computer-readable storage medium of claim 15, wherein the set of instructions, when executed by the processor, further causes the processor to determine an accuracy for the specialist.

18. The non-transitory computer-readable storage medium of claim 15, wherein the set of instructions, when executed by the processor, further causes the processor to determine an accuracy for the specialist by inserting at least one reference ECG in each ECG group.

19. The non-transitory computer-readable storage medium of claim 15, wherein the set of instructions, when executed by the processor, further causes the processor to extract a plurality of ECG features from the received ECG data.

20. The non-transitory computer-readable storage medium of claim 15, wherein the set of instructions, when executed by the processor, further causes the processor to categorize the ECG data into a plurality of groups based on extracted ECG features including location information.

21. The non-transitory computer-readable storage medium of claim 15, wherein the set of instructions, when executed by the processor, further causes the processor to categorize the ECG data into a plurality of groups based on extracted ECG features including user annotations.

22. The non-transitory computer-readable storage medium of claim 15, wherein the set of instructions, when executed by the processor, further causes the processor to categorize the ECG data into a plurality of groups based on extracted ECG features including one or more of: amplitude, polarity, duration, or shape of the P, Q, R, S and T waves and QRS complex; ratios and amplitude differences between P, Q, R, S and T waves, or QRS complex; beat to beat variability between P, Q, R, S and T waves, or QRS complex; P-R interval; QRS interval; Q-T interval; S-T interval; P-R segment; S-T segment; and beat to beat frequency.

23. The non-transitory computer-readable storage medium of claim 15, wherein the set of instructions, when executed by the processor, further causes the processor to notify a user that the user's ECG data has been interpreted.

24. The non-transitory computer-readable storage medium of claim 15, wherein the set of instructions, when executed by the processor, further causes the processor to store the ECG data and the interpreted ECG data in a database.

25. A non-transitory computer-readable storage medium storing a set of instructions capable of being executed by a processor, that when executed by the processor causes the processor to:
receive ECG data from a plurality of ECG recording devices;
categorize the ECG data into a plurality of groups based on extracted ECG features;
list the ECG groups by category on an online auction house;
receive bids for the listed ECG groups from registered specialists;
determine which specialist won a bid for a group from the listed ECG groups;
provide the specialist that won the bid for the group with access to the ECGs within the group; and
wherein the set of instructions, when executed by the processor, further causes the processor to provide a user with a list of local specialists based on location information provided with ECG data from the user.

26. A non-transitory computer-readable storage medium storing a set of instructions capable of being executed by a processor, that when executed by the processor causes the processor to:
receive ECG data from a plurality of ECG recording devices;
categorize the ECG data into a plurality of groups based on extracted ECG features;
list the ECG groups by category on an online auction house;
receive bids for the listed ECG groups from registered specialists;
determine which specialist won a bid for a group from the listed ECG groups;
provide the specialist that won the bid for the group with access to the ECGs within the group; and
wherein the set of instructions, when executed by the processor, further causes the processor to schedule an appointment for a user, using the processor, with a local specialist.

* * * * *